United States Patent
Kang et al.

(10) Patent No.: US 12,241,834 B2
(45) Date of Patent: Mar. 4, 2025

(54) ARTICLES AND METHODS FOR PERFORMING ASSAYS

(71) Applicant: Sartorius BioAnalytical Instruments, Inc., Bohemia, NY (US)

(72) Inventors: Tae Kang, Campbell, CA (US); Stewart Holloway, San Jose, CA (US); Michael Youngquist, Palo Alto, CA (US)

(73) Assignee: Sartorius BioAnalytical Instruments, Inc., Bohemia, NY (US)

( * ) Notice: Subject to any disclaimer, the term of this patent is extended or adjusted under 35 U.S.C. 154(b) by 0 days.

(21) Appl. No.: 18/579,324

(22) PCT Filed: Jul. 6, 2022

(86) PCT No.: PCT/US2022/036194
§ 371 (c)(1),
(2) Date: Jan. 12, 2024

(87) PCT Pub. No.: WO2023/287618
PCT Pub. Date: Jan. 19, 2023

(65) Prior Publication Data
US 2024/0280487 A1    Aug. 22, 2024

Related U.S. Application Data

(60) Provisional application No. 63/221,690, filed on Jul. 14, 2021.

(51) Int. Cl.
*G01N 21/64* (2006.01)

(52) U.S. Cl.
CPC ....... *G01N 21/6428* (2013.01); *G01N 21/645* (2013.01); *G01N 2021/6439* (2013.01);
(Continued)

(58) Field of Classification Search
CPC ............ G01N 21/6428; G01N 21/645; G01N 2021/6439; G01N 2021/6482; G01N 2021/6491; G01N 21/59; G01N 21/47; G01N 21/64; G01N 21/7703; G01N 2021/7709; G01N 2021/772; G01N 33/54373
(Continued)

(56) References Cited

U.S. PATENT DOCUMENTS

| | | |
|---|---|---|
| 4,447,546 A | 5/1984 | Hirschfeld |
| 7,319,525 B2 | 1/2008 | Tan et al. |

(Continued)

OTHER PUBLICATIONS

International Preliminary Report on Patentability (Chapter 2) for International Application No. PCT/US2022/036194 dated Nov. 21, 2023.
(Continued)

*Primary Examiner* — Christopher L Chin
(74) *Attorney, Agent, or Firm* — Wolf, Greenfield & Sacks, P.C.

(57) ABSTRACT

Instruments, components thereof, consumables therefor, and associated methods are generally provided. Advantageously, some instruments described herein may be capable of performing and/or configured to perform assays at a rate that is faster and/or requires less input from an operator than assays performed by other methods. Some methods may comprise performing assays at such faster rates and/or involving such reduced input.

23 Claims, 8 Drawing Sheets

(52) U.S. Cl.
CPC ............... *G01N 2021/6482* (2013.01); *G01N 2021/6491* (2013.01)

(58) Field of Classification Search
USPC ... 422/401, 407, 82.05, 82.08, 82.09, 82.11; 435/287.9, 288.7; 436/527, 172, 805, 436/809; 356/317, 318, 337, 432
See application file for complete search history.

(56) References Cited

U.S. PATENT DOCUMENTS

| | | |
|---|---|---|
| 7,394,547 B2 | 7/2008 | Tan et al. |
| 7,445,887 B2 | 11/2008 | Zuk et al. |
| 7,656,536 B2 | 2/2010 | Tan et al. |
| 7,728,982 B2 | 6/2010 | Tan et al. |
| 8,305,585 B2 | 11/2012 | Tan et al. |
| 8,647,588 B2 | 2/2014 | Recknor et al. |
| 9,046,485 B2 | 6/2015 | Salerno et al. |
| 2014/0322819 A1 | 10/2014 | Witte et al. |

OTHER PUBLICATIONS

International Search Report and Written Opinion for International Application No. PCT/US2022/036194 dated Oct. 11, 2022.
Wang et al., Development of combination tapered fiber-optic biosensor dip probe for quantitative estimation of interleukin-6 in serum samples. J Biomed Opt. Nov. 2010-Dec. 15(6):067005. doi: 10.1117/1.3523368.

100

ARTICLES AND METHODS FOR PERFORMING ASSAYS

RELATED APPLICATIONS

This Application is a national stage filing under 35 U.S.C. 371 of International Patent Application Serial No. PCT/US2022/036194, filed Jul. 6, 2022, entitled "Articles and Methods for Performing Assays", which claims priority under 35 U.S.C. § 119 (e) to U.S. Provisional Application No. 63/221,690, filed Jul. 14, 2021, and entitled "Articles and Methods for Performing Assays," the entire disclosure of each of which is incorporated herein by reference in its entirety for all purposes.

FIELD

Instruments for performing assays, and associated methods, are generally described.

BACKGROUND

Assays generally require the performance of a number of sequential steps and are typically performed in multi-well plates. Performing such steps in wells positioned in multi-well plates may require an appreciable amount of effort and/or time. Much of the effort and/or time may require the manual labor of an operator, which may result in delays, operator-induced variability, and/or operator-induced failures.

One type of assay that may require a particularly large input of operator effort and/or time to perform in a multi-well plate is an ELISA assay. In such assays, the operator may need to perform some or all of the following steps: (1) preparing the multi-well plate in which the assay is to be performed, which may involve coating it with a capture antibody, incubating the multi-well plate overnight, washing the multi-well plate, blocking the multi-well plate, and/or removing any excess liquid accumulated in one of the foregoing steps; (2) reacting samples and/or standards with the prepared multi-well plate, which may include pipetting the samples and/or standards into the plates in the multi-well plate, incubating the multi-well plate, washing the multi-well plate, and/or removing any excess liquid accumulated in one of the foregoing steps; (3) reacting further reagents with the samples and/or standards to yield detectable signals, which may include adding a detection antibody solution to the wells in the multi-well plate, incubating the multi-well plate, adding an enzyme-linking solution to the wells in the multi-well plate, incubating the multi-well plate, washing the multi-well plate, adding a chromogenic substrate to each well in the multi-well plate, and/or adding a stop solution to each well in the multi-well plate; and/or (4) measuring an optical signal from the multi-well plate.

Accordingly, new instruments and methods for performing assays are needed.

SUMMARY

The present disclosure generally describes articles and methods for performing assays. The subject matter described herein involves, in some cases, interrelated products, alternative solutions to a particular problem, and/or a plurality of different uses of one or more systems and/or articles.

In some embodiments, an instrument for performing an assay is provided. The instrument for performing the assay comprises a probe, a support structure positioned proximal to the probe, and an optical detector configured to detect an optical signal. A reagent is immobilized on the probe. The probe is configured to be translated by the instrument between a plurality of locations at which a plurality of fluids is positioned. The optical signal comprises light that has been emitted, transmitted, reflected, and/or scattered from a species immobilized on the probe, light that has been emitted, transmitted, reflected, and/or scattered from a species generated from a species immobilized on the probe, the absence of light due to absorption of light by a species immobilized on the probe, and/or the absence of light due to absorption of light by a species generated from a species immobilized on the probe.

In some embodiments, an instrument for performing an assay comprises a probe, a support structure positioned proximal to the probe, and an optical detector configured to detect an optical signal. The probe is configured to transmit light. A reagent is immobilized on the probe. The probe is configured to be translated by the instrument between a plurality of locations at which a plurality of fluids is positioned. The optical signal comprises light that has been emitted, polarized and/or scattered from a species immobilized on the probe, light that has been emitted, polarized and/or scattered from a species generated from a species immobilized on the probe, the absence of light due to absorption of light by a species immobilized on the probe, and/or the absence of light due to absorption of light by a species generated from a species immobilized on the probe.

In some embodiments, an instrument for performing an assay comprises a housing, an optical cable, and an optical detector configured to detect an optical signal. The housing comprises a component configured to receive a probe. The housing comprises a support structure positioned proximal to the component configured to receive the probe. The support structure is configured to receive a container for one or more fluids. The instrument is configured to translate the probe between a plurality of locations proximal to a plurality of locations in the container. The optical cable transmits the light to the optical detector. The optical signal comprises light that has been emitted, transmitted, reflected, and/or scattered from a species immobilized on the probe, light that has been emitted, transmitted, reflected, and/or scattered from a species generated from a species immobilized on the probe, the absence of light due to absorption of light by a species immobilized on the probe, and/or the absence of light due to absorption of light by a species generated from a species immobilized on the probe.

In some embodiments, an instrument for performing an assay comprises a housing, a probe, and an optical detector configured to detect an optical signal. The housing comprises a component configured to receive the probe. The probe is configured to transmit light. A reagent is immobilized on the probe. The housing comprises a support structure positioned proximal to the component configured to receive the probe. The support structure is configured to receive a container for one or more fluids. The instrument is configured to translate the probe between a plurality of locations proximal to a plurality of locations in the container. The optical signal comprises light that has been emitted, polarized, and/or scattered from a species immobilized on the probe, light that has been emitted, polarized, and/or scattered from a species generated from a species immobilized on the probe, the absence of light due to absorption of light by a species immobilized on the probe, and/or the absence of light due to absorption of light by a species generated from a species immobilized on the probe.

In some embodiments, an instrument for performing an assay comprises a probe, a support structure positioned proximal to the probe, and an optical detector configured to detect an optical signal. A reagent is immobilized on the probe. The support structure is configured to be translated by the instrument such that a plurality of portions of the support structure are sequentially positioned proximal to the probe. The optical signal comprises light that has been emitted, transmitted, reflected, and/or scattered from a species immobilized on the probe, light that has been emitted, transmitted, reflected, and/or scattered from a species generated from a species immobilized on the probe, the absence of light due to absorption of light by a species immobilized on the probe, and/or the absence of light due to absorption of light by a species generated from a species immobilized on the probe.

In some embodiments, an instrument for performing an assay comprises a probe, a support structure positioned proximal to the probe, and an optical detector configured to detect an optical signal. The probe is configured to transmit light. A reagent is immobilized on the probe. The support structure is configured to be translated by the instrument such that a plurality of portions of the support structure are sequentially positioned proximal to the probe. The optical signal comprises light that has been emitted, polarized, and/or scattered from a species immobilized on the probe, light that has been emitted, polarized, and/or scattered from a species generated from a species immobilized on the probe, the absence of light due to absorption of light by a species immobilized on the probe, and/or the absence of light due to absorption of light by a species generated from a species immobilized on the probe.

In some embodiments, an instrument for performing an assay comprises a housing, a probe, and an optical detector configured to detect an optical signal. The housing comprises a component configured to receive a probe. The housing comprises a support structure positioned proximal to the component configured to receive the probe. The support structure is configured to receive a container for one or more fluids. The support structure is configured to be translated by the instrument such that a plurality of locations in the container are sequentially positioned proximal to the probe when the probe is positioned in the component. The optical cable transmits the light to the optical detector. The optical signal comprises light that has been emitted, transmitted, reflected, and/or scattered from a species immobilized on the probe, light that has been emitted, transmitted, reflected, and/or scattered from a species generated from a species immobilized on the probe, the absence of light due to absorption of light by a species immobilized on the probe, and/or the absence of light due to absorption of light by a species generated from a species immobilized on the probe.

In some embodiments, an instrument for performing an assay comprises a housing, a probe, and an optical detector configured to detect an optical signal. A reagent is immobilized on the probe. The housing comprises a component configured to receive a probe. The housing comprises a support structure positioned proximal to the component configured to receive the probe. The support structure is configured to receive a container for one or more fluids. The support structure is configured to be translated by the instrument such that a plurality of locations in the container are sequentially positioned proximal to the probe when the probe is positioned in the component. The optical signal comprises light that has been emitted, polarized, and/or scattered from a species immobilized on the probe, light that has been emitted, transmitted, reflected, and/or scattered from a species generated from a species immobilized on the probe, the absence of light due to absorption of light by a species immobilized on the probe, and/or the absence of light due to absorption of light by a species generated from a species immobilized on the probe.

In some embodiments, a method of performing an assay is provided. The method comprises sequentially contacting a probe with a plurality of fluids and detecting an optical signal. A reagent is immobilized on the probe. The optical signal comprises light that has been emitted, transmitted, reflected, and/or scattered from a species immobilized on the probe, light that has been emitted, transmitted, reflected, and/or scattered from a species generated from a species immobilized on the probe, the absence of light due to absorption of light by a species immobilized on the probe, and/or the absence of light due to absorption of light by a species generated from a species immobilized on the probe.

In some embodiments, a method comprises providing a probe, providing a container for one or more fluids, and detecting an optical signal. A reagent is immobilized on the probe. Light is transmitted through one or more apertures on the probe. The optical signal comprises light that has been emitted, polarized, and/or scattered from a species immobilized on the probe, light that has been emitted, polarized, and/or scattered from a species generated from a species immobilized on the probe, the absence of light due to absorption of light by a species immobilized on the probe, and/or the absence of light due to absorption of light by a species generated from a species immobilized on the probe.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
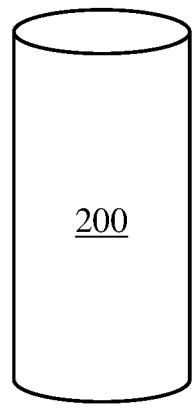
FIG. 1A is a schematic depiction of an instrument, in accordance with some embodiments.
Figure 1A:
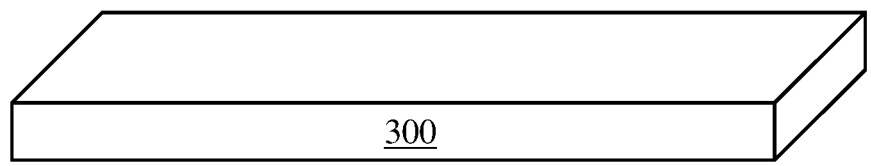
Figure 1A:
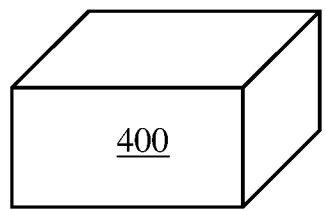

Instruments, components thereof, consumables therefor, and associated methods are generally provided. Advantageously, some instruments described herein may be capable of performing and/or configured to perform assays at a rate that is faster, requires less input from an operator, and/or uses a smaller sample volume than assays performed by other methods. Some methods may comprise performing assays at such faster rates, involving such reduced input, and/or using such smaller sample volumes.

Some instruments described herein may comprise a probe and/or be configured to receive a probe. Advantageously, the probe may be capable of and/or configured to translate between a plurality of locations, such as locations at which fluids are positioned. The fluids may be fluids suitable for performing an assay. Relatedly, in some embodiments, a probe may be employed to perform an assay by sequentially contacting a plurality of fluids comprising a sample, one or more fluids comprising a reagent, and, optionally, one or more wash fluids. The probe may be capable of contacting these fluids in a manner that is relatively rapid (e.g., in comparison to methods of contacting fluids performed by an operator and/or in comparison to instruments having designs other than those described herein). For instance, the fluids can initially be positioned in a container or containers supported by a support structure (e.g., wells in a multi-well plate), and the probe can be incubated with each such fluid sequentially. Sequentially incubating the probe in a plurality of environments may be relatively efficient because it may allow for shortened incubation times and/or eliminate the need to perform manual washing steps.

In some embodiments, a probe suitable for use with an instrument described herein is functionalized. The functionalization may comprise the immobilization of a reagent thereon, such as a reagent employed in an assay. Advantageously, the use of functionalized probes may eliminate the time and/or labor associated with the functionalization of a substrate on which an assay is to be performed prior to the performance of the assay. When employed, such functionalized probes may also be relatively easy to attach and/or detach from the instrument. This may allow for rapid and/or automated probe exchange, which may further promote the performance of efficient assays that require reduced input from operators.

Some instruments described herein are suitable for performing assays that stop one or more reactions mechanically. Similarly, some methods described herein comprise performing an assay that stops one or more reactions mechanically. This may be accomplished by, for instance, removing a probe on which a reagent is immobilized from contact with a fluid comprising a reagent reacting therewith. Stopping a reaction mechanically may advantageously eliminate the need for a stop reagent and/or stop solution. Performing assays without the use of stop reagents and stop solutions (or with fewer stop reagents and stop solutions) may advantageously reduce the number of fluids and reagents needed to perform an assay and/or allow for more precise control over when reactions are stopped.

Some instruments described herein are capable of performing assays with enhanced reproducibility. Similarly, some methods described herein comprise performing assays with enhanced reproducibility. The enhanced reproducibility may result from increased automation and/or the presence of a reduced number of steps performed by an operator. Advantageously, the enhanced reproducibility may reduce run-to-run variation and/or failures.

Some instruments described herein are capable of performing assays that comprise performing an agitation step and/or a mixing step. Similarly, some methods described herein comprise performing assays that comprise performing an agitation step and/or a mixing step. Such steps may comprise agitating and/or mixing a fluid with which a probe is in contact, with which a probe will be in contact, and/or with which a probe was in contact. In some embodiments, an agitation step and/or a mixing step comprises employing a probe to stir a fluid with which it is in contact, thereby agitating and/or mixing the fluid. Agitation steps and mixing steps may be particularly well-suited for increasing the rate at which species in a fluid contact species immobilized on a probe and/or for homogenizing the fluid with which a probe is in contact. Advantageously, such methods may thereby enhance the rate of one or more reactions that occurs during assay performance.

In some embodiments, an instrument described herein is suitable for performing an assay that results in an optical signal and/or a method described herein comprises producing an optical signal. In such embodiments, the instrument may be configured to detect the optical signal and/or the method may comprise generating and/or detecting the optical signal. The optical signal may be indicative of a feature of the sample and/or a result of an assay. For instance, in some embodiments, an optical signal comprises emitted, transmitted, reflected, scattered, polarized, and/or absorbed light that is indicative of a feature of the sample and/or a result of an assay. In some embodiments, the optical signal is generated by a species associated with a probe. As an example, the optical signal may comprise light emitted, transmitted, reflected, scattered, polarized, and/or absorbed by a species immobilized on a probe. As another example, the optical signal may comprise light that is emitted, transmitted, reflected, scattered, polarized, and/or absorbed by a species that is generated from a species immobilized on a probe. For instance, a species immobilized on the probe may react with a species present in a fluid with which it is in contact to generate a species that emits and/or absorbs light, and the optical signal may comprise light emitted, transmitted, reflected, scattered, polarized, and/or absorbed by that species.

In some embodiments, an optical signal is detected and/or generated while a probe is in contact with a fluid (e.g., a fluid in which a species immobilized on the probe is initially present, a fluid in which a species generated from a species immobilized on the probe is generated, a fluid from which the optical signal arises, a fluid in which the probe is incubated). Some optical signals that are detected and/or generated while a probe is in contact with a fluid may be well-suited for use in kinetic measurements (e.g., a series of measurements taken at two or more times during a reaction) and/or pulse measurements (e.g., measurements performed during flash luminescence and/or flash reactions). In some embodiments, an optical signal is read at the point in time at which a probe is first contacted with a fluid.

The ability to detect optical signals arising from a variety of locations (e.g., proximal to the probe, from a fluid in which the probe is incubated with and/or has been incubated with) may allow for the detection of optical signals arising in a variety of ways. This may allow the instruments described herein to be suitable for performing a variety of assays. For instance, as described above, an instrument may be suitable for detecting an optical signal arising from a probe and/or from a fluid and/or species therein. Desirably, this may allow for the detection of optical signals from assays in which the species generating the signal is immobilized on the probe (e.g., by reaction with a species initially immobilized on the probe and/or initially present in the sample) and/or from assays in which the species generating the signal is formed in a fluid with which the probe is in contact (e.g., the species may be generated from a species immobilized on a probe). The latter scenario may be particularly useful for assays in which an enzyme is employed that catalyzes a reaction producing a species generating an optical signal.

Some instruments described herein are suitable for performing assays that comprise binding reactions. Similarly, some methods described herein comprise performing an assay that comprises a binding reaction. Some such binding reactions may have very high sensitivity, which may advantageously allow for assays to be performed on samples having smaller volumes and/or including analytes at relatively low concentrations. The sensitivity of a binding reaction may be facilitated by mixing and/or agitating a fluid in which the binding reaction is occurring (e.g., a fluid in contact with a probe). In some instances, the sensitivity of a binding reaction is facilitated by the localization of the binding reaction to the probe, which may have a relatively small reaction surface.

In some embodiments, an instrument described herein is suitable for performing multiplexed analyses. Similarly, some methods described herein comprise performing a multiplexed analysis. The multiplexed analysis may take the form of performing two or more different assays on a single sample and/or detecting two or more different analytes present in a single sample. This may be facilitated by the use of different probes upon which different reagents are immobilized. In some embodiments, the result of the assay and/or the detection of the analyte may be quantitative. Multiplexed analyses may advantageously allow for a relatively small volume of sample to be employed for the performance of multiple assays and/or the detection of multiple species.

In some embodiments, a system is capable of performing an assay and/or a method comprises performing an assay in which two or more different probes having the same surface chemistry (e.g., the same species immobilized thereon) are contacted with a common sample. The assay may comprise performing the same steps with both probes and/or detecting the same type of optical signal from both probes. Such assays may advantageously comprise performing multiple replicates on a common sample with different probes An overview of various components that may be included in the systems described herein and their arrangements are presented below. Further detail regarding suitable designs for specific components will be presented after this overview. One example of an instrument is shown in FIG. 1A. As depicted therein, the instrument 100 comprises a probe 200, a support structure 300, and an optical detector 400.

As described elsewhere herein, FIG. 1A and the other FIGS. in this application are not intended to be drawn to scale. Accordingly, an instrument may comprise a probe having a different shape than the shape of the probe shown in FIG. 1A, a support structure having a different shape than the support structure shown in FIG. 1A, and/or an optical detector having a different shape than the optical detector shown in FIG. 1A. Additionally, an instrument may comprise a probe, a support structure, and an optical detector that have different sizes with respect to each other than the relative sizes of the probe, support structure, and optical detector depicted in FIG. 1A. It should also be understood that this application contemplates instruments and/or components thereof having different shapes and/or relative sizes than those depicted in any of the FIGS. herein.

As shown in FIG. 1A, a support structure may be proximal to a probe. In some embodiments, the support structure is positioned beneath the probe. It is also possible for an instrument to comprise a support structure that is positioned proximal to the probe but not beneath the probe. For instance, in some embodiments, an instrument comprises a support structure that is positioned at the same height of the probe and/or above the probe. It is also possible for an instrument to comprise a support structure that is positioned beside the probe (e.g., at the same height as the probe, at a different height from the probe).

Figure 1B:
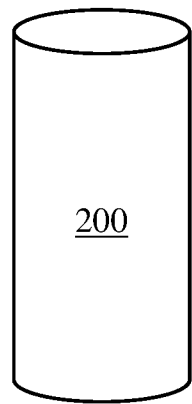
FIG. 1B is a schematic depiction of a support structure that supports a multi-well plate, in accordance with some embodiments.
Figure 1B:
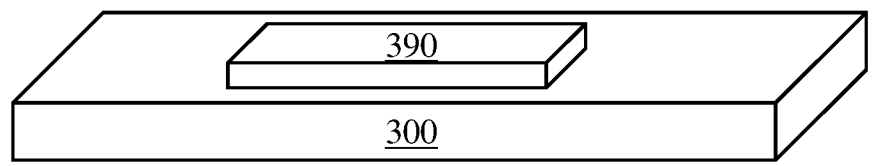
Figure 1B:
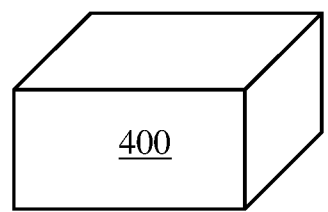

A support structure may be a structure that supports an article to be employed during use of the instrument. For instance, in some embodiments, a support structure supports a container for one or more fluids employed during an assay. Non-limiting examples of such containers include multi-well plates, microtiter plates, glass slides, droplet arrays, vials, microfluidic devices, microfluidic arrays, microarrays, and digital microfluidic chips. The support structure may support such articles in a variety of ways. As one example, in some embodiments, an instrument comprises a support structure that is positioned and/or configured to be positioned beneath one or more such articles. It is also possible for a support structure to support such articles by clamping them in place, partially or fully surrounding them laterally, and/or suspending them. FIG. 1B shows one non-limiting example of a support structure that supports a multi-well plate by being positioned beneath it. In FIG. 1B, a multi-well plate 390 is positioned on top of the support structure in the instrument shown in FIG. 1A. FIG. 1B also shows the instrument 100 comprising a probe 200, a support structure 300, and an optical detector 400

As will be described in further detail below, in some embodiments, an instrument comprises a probe that is configured to be translated by the instrument and/or a support structure that is configured to be translated by the instrument. In such embodiments, the positioning of the probe with respect to the support structure may change over time. For instance, the instrument may have a resting state or storage state in which the probe and the support structure are positioned in a pair of first locations and an active state in which the support structure and/or the probe are positioned in different locations than in the resting state or storage state. As another example, in some embodiments, an instrument may be configured to translate a support structure and/or a probe during use. In such embodiments, the support structure and/or the probe may be positioned in a plurality of locations and/or moved between locations.

As described above, it is also possible for an instrument to comprise both a stationary probe and a stationary support structure.

As also shown in FIGS. 1A and 1B, an instrument may comprise an optical detector, such as an optical detector configured to detect an optical signal. The positioning of the optical detector may generally be selected as desired. In some embodiments, like the embodiment shown in FIGS. 1A and 1B, the optical detector is positioned proximal to a support structure and/or a probe (e.g., on an opposite side of the support structure from the probe, on the same side of the support structure as the probe). It is also possible for an optical detector to be positioned distal to a support structure and/or a probe. In such embodiments, the optical detector may be optically coupled to a location at which an optical signal is generated. For instance, in some embodiments, an optical cable may transmit light (e.g., light that is an optical signal, light that indicates the absence of an optical signal) from a location proximal to the location at which the optical signal is generated to the optical detector. Some instruments may comprise two or more optical detectors (e.g., one positioned proximal to a support structure and one positioned proximal to a probe, two positioned proximal to two different probes).

Without wishing to be bound by any particular theory, it is believed that optical detectors positioned on an opposite side of a support structure from a probe and/or optically coupled to such a location may be particularly suitable for detecting optical signals comprising the absence of light (e.g., due to absorption, reflection, and/or scattering). Similarly, and also without wishing to be bound by any particular theory, it is believed that optical detectors positioned at such locations may also be particularly suitable for detecting optical signals comprising transmitted light. As a third example, and also without wishing to be bound by any particular theory, it is believed that optical detectors positioned on an opposite side of a support structure from a probe, optical detectors positioned on the same side of a support structure as a probe, and/or optical detectors optically coupled to either such location be suitable for detecting optical signals comprising emitted light, reflected light, scattered light, and/or polarized light.

Figure 2:
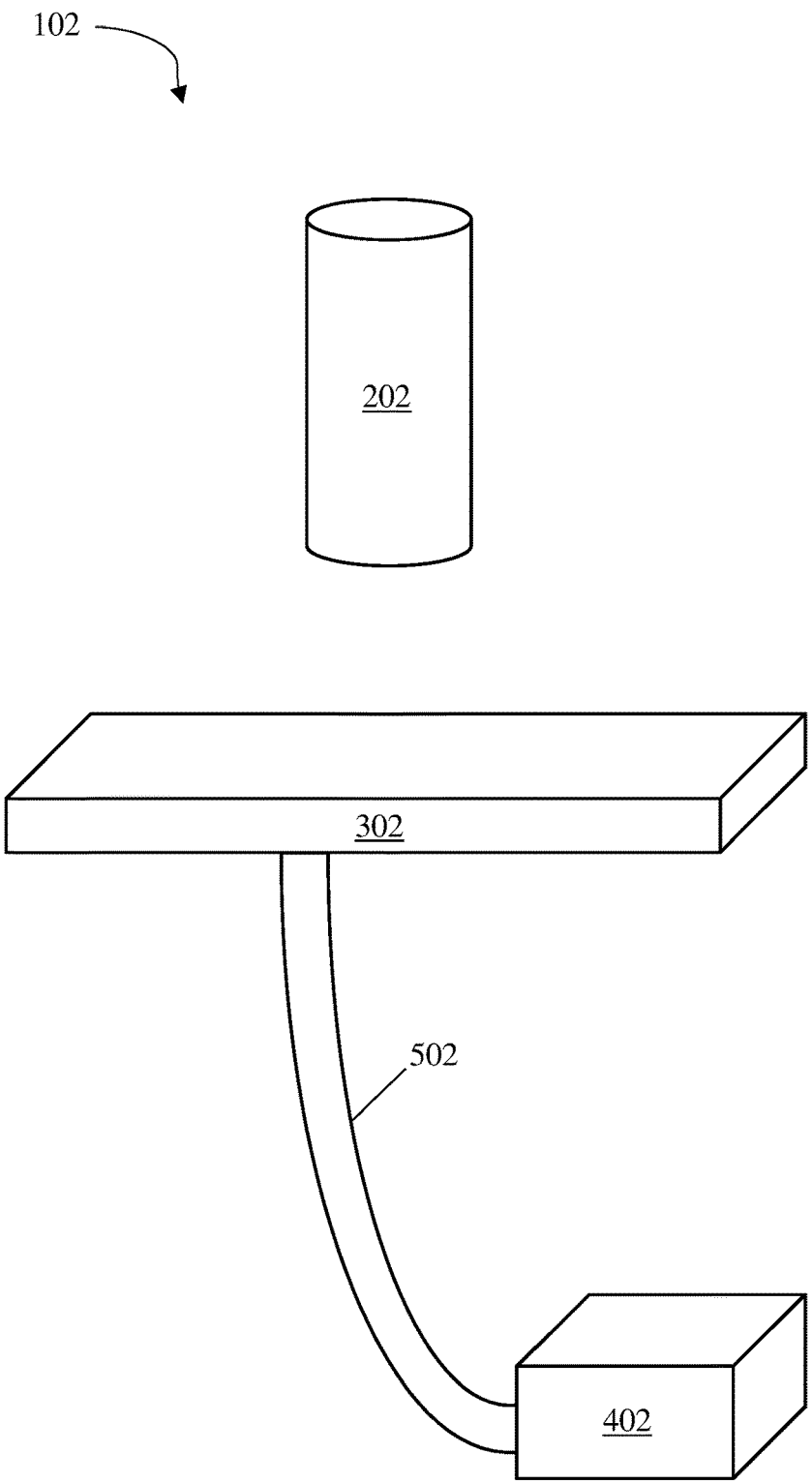
FIGS. 2 and 3 are schematic depictions of instruments comprising optical cables, in accordance with some embodiments.
Figure 3:
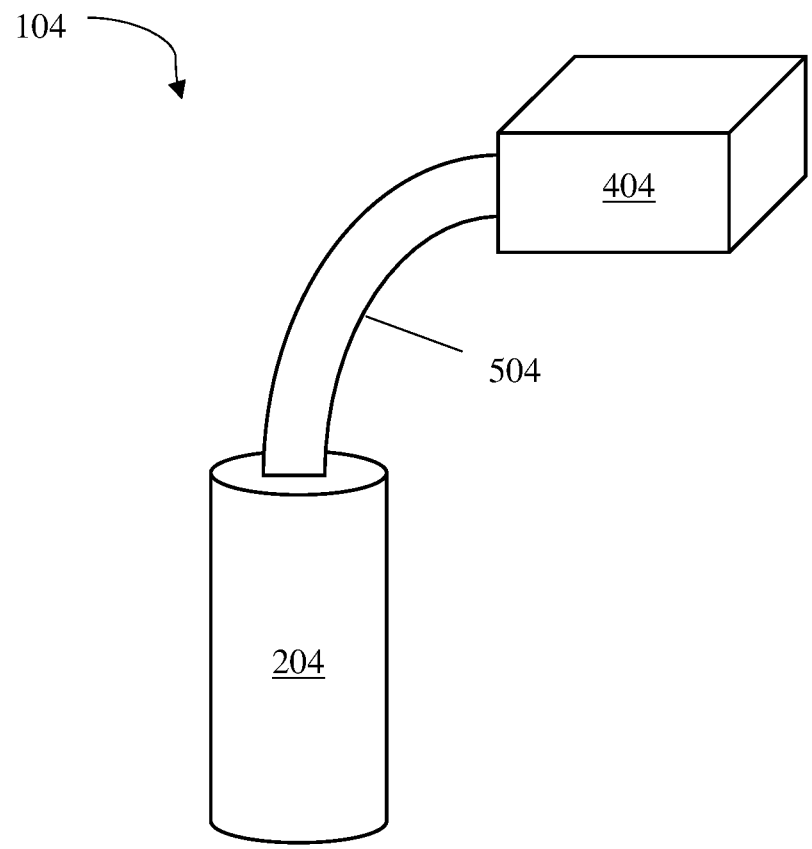

FIGS. 2 and 3 show two examples of instruments comprising optical cables that are configured to transmit light from a location proximal to the location at which the optical signal is generated to the optical detector. In FIG. 2, the optical cable 502 is configured to transmit light to the optical detector 402. Similarly, in FIG. 3, the optical cable 504 is configured to transmit light from the probe 204 to the optical detector 404. FIG. 2 further depicts an instrument 102 comprising the optical cable 502. The instrument 102 further comprises a probe 202, a support structure 302, and the optical detector 402. FIG. 3 further depicts an instrument 104 comprising the optical cable 504. The instrument 104 further comprises the probe 204, a support structure 304, and the optical detector 404.

Embodiments like those shown in FIG. 2 may be suitable for performing assays in which the species generating the optical signal is present in a fluid that the probe may contact. In FIG. 2, the optical cable transmits light from a location proximal to the support structure to the optical detector. The support structure may serve as a support for a container for a fluid in which the optical signal is generated. Additionally, in some such embodiments, the probe is not coupled to the detector by an optical cable.

Embodiments like those shown in FIG. 3 may be suitable for performing assays in which the species generating the optical signal is immobilized on the probe, as the optical cable is configured to transmit light from the probe to the optical detector. In some such embodiments, any fluid with which the probe is in contact is not coupled to the optical detector by an optical cable. It is also possible for neither the probe nor any fluid with which it is in contact to be coupled to the optical detector by an optical cable. For instance, an embodiment may comprise an optical detector positioned such that it can directly receive an optical signal from the probe and/or the fluid without the need for an optical cable positioned therebetween. It is also possible for an instrument to comprise further optics that assist with the collection of light by an optical detector. As an example, an instrument may comprise one or more lenses configured for this purpose.

Some instruments comprising two or more optical detectors may comprise one optical cable configured to transmit light in a manner similar to the manner shown in FIG. 2 and one optical cable configured to transmit light in a manner similar to the manner shown in FIG. 3. It is also possible for an instrument to comprise an optical detector that is not in optical communication with an optical cable. As an example, an optical detector may be positioned at a distance from the source and/or at an angle thereto such that it is capable of collecting an optical signal of sufficient strength for an assay without the assistance of an optical cable.

Figure 4:
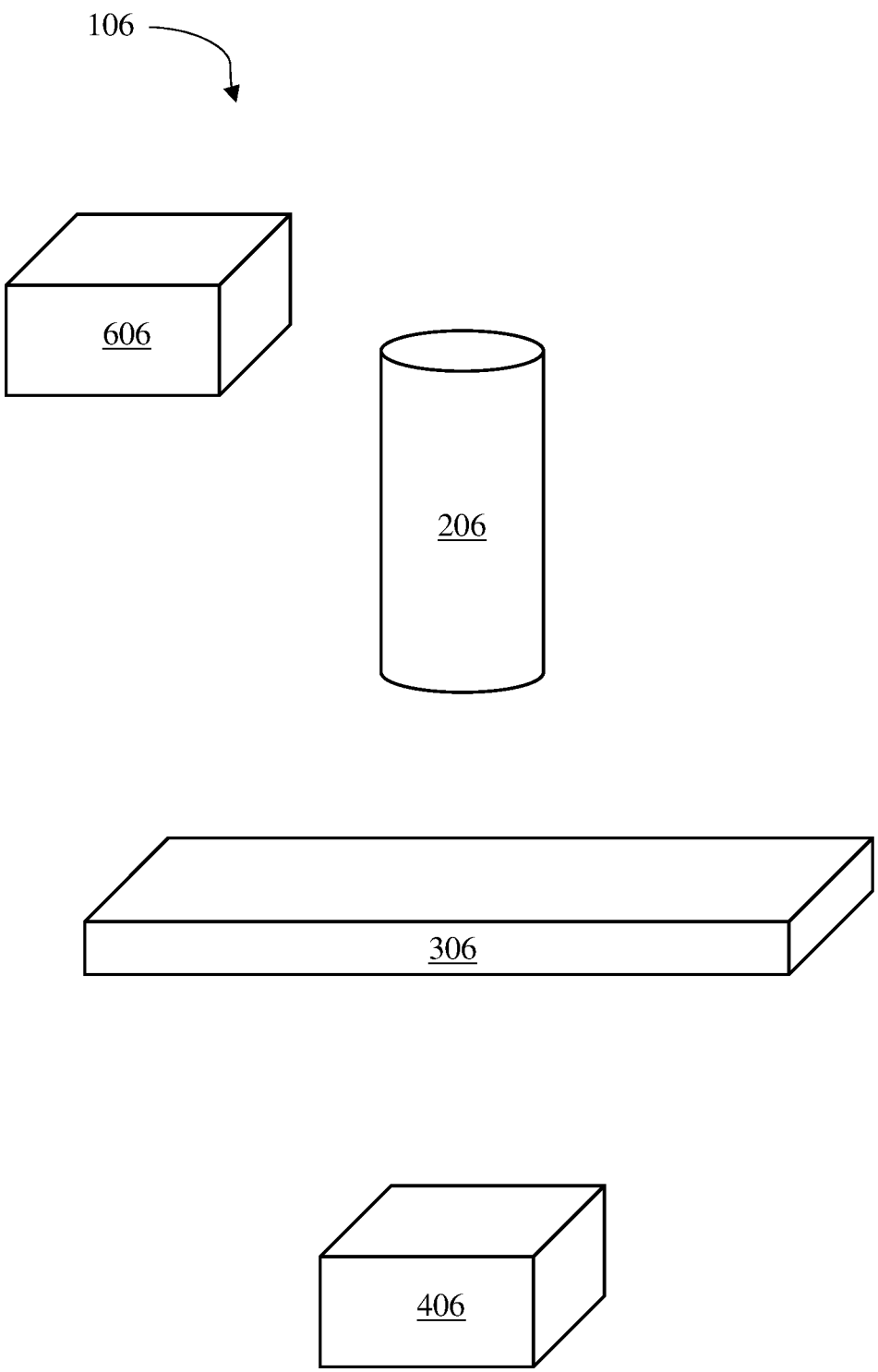
FIG. 4 is a schematic depiction of an instrument that comprises a light source, in accordance with some embodiments.

In some embodiments, an instrument comprises a light source. FIG. 4 shows a schematic depiction of one such embodiment. In FIG. 4, the instrument 106 comprises a probe 206, a support structure 306, an optical detector 406, and a light source 606. The light source may provide light to the instrument. In some embodiments, the light may be light employed in the formation of the optical signal. For instance, in embodiments in which the optical signal is fluorescent light, the light provided by the light source may be light that excites the emission of fluorescent light. As another example, in embodiments in which the optical signal is light that has been scattered (e.g., Raman scattered), the light may be light that generates the scattering (e.g., Raman scattering). As a third example, in embodiments in which the optical signal is light that has been transmitted, the light may be light that is transmitted through one or more fluids present in the assay. As a fourth example, in embodiments in which the optical signal is light that has been reflected, the light is light that is reflected by one or more fluids present in the assay. As a fifth example, in embodiments in which the optical signal is the absence of light due to absorption, the light may be light that is absorbed by a species present in the assay. As a sixth example, in embodiments in which the optical signal is light that has been polarized, the light may be light that is unpolarized or light that has a polarization that is affected by a species present in the assay.

Figure 5:
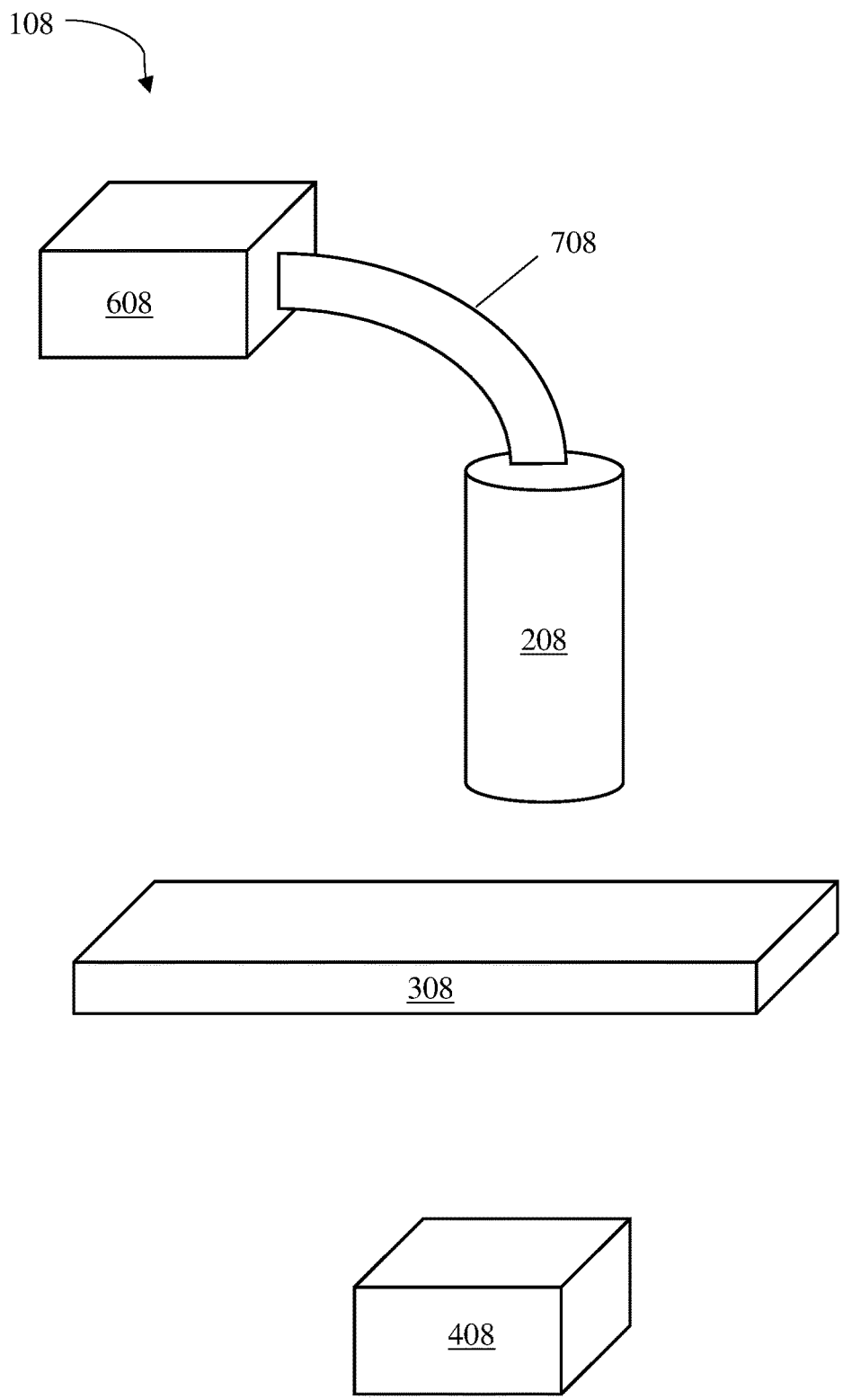
FIG. 5 is a schematic depiction of an instrument that comprises a light source, a probe, an optical cable, in accordance with some embodiments.

In some embodiments, an instrument comprises a light source and comprises an optical cable that is configured to transmit light from the light source to the probe. In such embodiments, the probe may illuminate one or more portions of the instrument and/or one or more fluids present in an assay being performed by the instrument. FIG. 5 shows a schematic depiction of such an instrument. In FIG. 5, the instrument 108 comprises a probe 208, a support structure 308, an optical detector 408, a light source 608, and an optical cable 708. The optical cable 708 in FIG. 5 is configured to transmit light from the light source 608 to the probe 208.

Figure 6:
FIG. 6 is a schematic depiction of an instrument that comprises a housing, in accordance with some embodiments.
Figure 6:
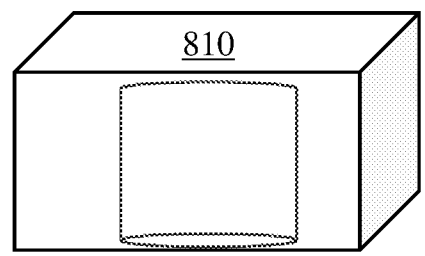
Figure 6:
Figure 6:
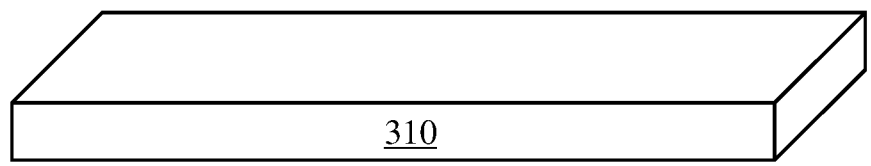
Figure 6:
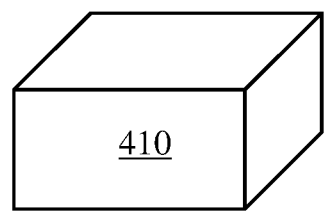

It should be understood that some instruments may have a design that comprises some of the features shown in two or more different figures shown herein. For instance, in some embodiments, an instrument comprises an optical cable configured to transmit light to an optical detector (e.g., as shown in FIG. 2 and/or FIG. 3) and further comprises a light source and/or a second optical cable configured to transmit light from the light source to the probe (e.g., as shown in FIG. 4 and/or FIG. 5). It is also possible for an instrument to have a design like that shown in one or more of FIGS. 1-5 but lack a probe. In such embodiments, the instrument may be configured to receive a probe. As an example, in some embodiments, an instrument comprises a housing comprising a component configured to receive a probe. FIG. 6 shows one non-limiting example of an instrument with this design.

In FIG. 6, the instrument 110 comprises a support structure 310, an optical detector 410, and a housing 810. The housing 810 comprises a component 910 configured to receive a probe. In such instruments, a probe may be positioned in the housing during use of the instrument.

Probes may be received in components of housings in a variety of suitable manners. In some embodiments, the component configured to receive the probe may be an opening and the probe may be inserted into the opening. Additionally or alternatively, it is also possible for a probe to be mechanically coupled to a component (e.g., by use of clamps).

It is also possible for a device described herein to comprise two or more sets of certain components. As an example, in some embodiments, an instrument comprises two or more probes (e.g., positioned in different locations from each other). In some such embodiments, two or more of the probes present in an instrument may be configured to be translated. The instrument may be configured to translate the two or more probes independently from each other and/or to translate them together. As one example of the latter type of translation, two or more optical probes may be positioned at constant distances from each other and both or all translated in a manner such that these constant distances are maintained while the probes move. As one example of the former translation, two or more optical probes may be translated with respect to each other such that the motion of one optical probe does not affect the motion of any other optical probe from which it is independently translated.

Additionally, when present, two or more probes may be translated across different locations and/or different sets of locations from each other. This may advantageously allow different optical probes to perform different assays and/or to perform different parts of a single assay, which may beneficially increase throughput in comparison to an instrument including only a single probe or including multiple probes that are translated across a common location or set of locations. However, it is also possible for an instrument to comprise two or more probes that are translated across a common location or set of locations. As an example, in some embodiments, two or more probes that have the same surface chemistry (e.g., the same reagent immobilized thereon) may be translated across a sample and/or a common set of locations (of which at least one is a location in contact with a sample). This may advantageously allow for multiple measurements of the same analyte and/or multiple replicates of the same assay to be performed on a common sample.

As described above, instruments comprising two or more probes may be particularly suitable performing two or more assays (e.g., sequentially, simultaneously, during periods of time that overlap, during periods of time that do not overlap). In such embodiments, each probe may be configured to perform an assay independently of the other probe. The assays may be of the same type (e.g., performed on different samples) or of different types (e.g., performed to determine two or more different properties of a single sample). In some such embodiments, two or more probes are contacted with a common sample to perform a multiplexed assay on that sample and/or to detect two or more different analytes in that sample.

It is also possible for such instruments to be used in the performance of a single assay. In such embodiments, the different probes may be employed to perform different aspects for the assay. For instance, one probe may be employed to perform the assay on a sample and one or more additional probes may be employed to perform the assay on one or more standards. In some embodiments, the presence of two probes and/or two components configured to receive probes may allow for rapid exchange of probes and/or the performance of an assay with one probe while another probe is loaded and/or prepared. In some embodiments, the different probes may be employed to perform replicates of the same assay.

It is also possible for an instrument to comprise two or more sets of components other than probes. For instance, an instrument may comprise two or more locations in a housing in which probes are configured to be received, two or more support structures, two or more light sources, and/or two or more optical detectors. As another example, in some embodiments, an instrument comprises two or more of the instruments shown in FIGS. 1-6. When an instrument comprises two or more probes and/or two or more locations in a housing in which probes are configured to be received, it may be beneficial for the instrument to further comprise two or more optical detectors. Each optical detector may be configured to detect an optical signal arising from a species associated with a different probe (e.g., a species immobilized on a probe, a species generated from a species immobilized on a probe). In some such embodiments, a common light source may be employed that is configured to supply light to all of the probes. This may be particularly suitable for instruments in which a single assay is performed at once and/or in which multiple assays of a single type are performed at once. It is also possible for an instrument comprising two or more probes and/or two or more locations in a housing in which probes are configured to be received to comprise two or more light sources (e.g., a light source associated with each probe). Such instruments may be particularly suitable for embodiments in which the instrument is configured to perform two or more different types of assays simultaneously.

As described above, in some embodiments, an instrument comprises a probe and/or comprises a housing configured to receive a probe. The probe may serve as a substrate upon which an assay can be performed and/or may assist with the detection of one or more optical signals generated during an assay.

In some embodiments, an instrument comprises a probe that is an optical probe. For instance, the instrument may comprise a probe that is part of one or more optical pathways therein and/or that is configured to transmit light. It is also possible for an instrument to comprise a probe that is not an optical probe. Probes that are not optical probes may be positioned outside of any optical pathways present in the instrument and/or may transmit very low amounts (or zero) light. For instance, an instrument may comprise a first optical cable that transmits light from a location proximal to a support structure to an optical detector and comprise a second optical cable that transmits light from a light source to a location proximal to a support structure. As another example, an instrument may comprise an optical cable that transmits light from a location proximal to a support structure to an optical detector and may lack a light source. In other words, in some embodiments, a probe is not an optical probe and the transmission of light to and from a location proximal to a support structure is not performed and/or is accomplished by a pathway that does not pass through the probe. As described in further detail elsewhere herein, some instruments may comprise two or more probes. In such embodiments, the instrument may comprise one or more optical probes and/or one or more probes that are not optical probes. Similarly, instruments may comprise exclusively optical probes, exclusively probes that are not optical probes, or both optical probes and non-optical probes.

As described above, in some embodiments, a probe is configured to transmit light. In such embodiments, the probe may transmit light in a manner that facilitates the analysis of an assay. For instance, some probes may transmit light from a light source to a location proximal to the probe, such as to a location in which a species immobilized on the probe is positioned and/or a fluid that is located proximal to the probe. In such embodiments, the light may be light that is transmitted to the probe from a light source (e.g., by an optical cable). The light may be light that facilitates the formation of an optical signal. For instance, the light may be light that will be absorbed, be transmitted, be reflected, be scattered (e.g., by Raman scattering), be polarized, and/or excite fluorescence to generate an optical signal that can be detected by an optical detector.

In some embodiments, a probe transmits light from a location proximal to the probe to an optical cable. In such embodiments, the light may be transmitted by the optical cable to an optical detector. As one example, the light may be light that is generated by a species proximal to the probe (e.g., immobilized on the probe, present in a fluid contacting the probe). As another example, the light may be light that is transmitted from a fluid positioned proximal to the probe to the detector. In such embodiments, the light may be light that forms an optical signal. For instance, the light may be light that has not been absorbed, light that has been transmitted, light that has been reflected, light that has been scattered (e.g., by Raman scattering), light that has been generated by fluorescence, and/or light that has been generated by luminescence (e.g., chemiluminescence).

The probe may have a variety of suitable designs. In some embodiments, the probe is a fiber-optic probe and/or comprises an optical fiber. It is also possible for a probe to include two or more optical fibers. For instance, a probe may comprise a fiber-optic bundle. In some embodiments, the probe comprises one or more apertures through which light may be transmitted. For instance, a probe may comprise a plurality of optical fibers, and the terminus of each optical fiber may serve as an aperture through which light may be transmitted. When present, the apertures may be positioned on a side of the probe opposite a side on which any optical cables are positioned. In such embodiments, the probe may serve to transmit light from an optical cable to an aperture and/or to transmit light from an aperture to an optical cable.

It is also possible for a probe to comprise further optics (e.g., in addition to optical fibers) that assist with the transmission of light. As an example, a probe may comprise a lens and/or a pinhole. When present, these components may assist with near-field imaging. In some embodiments, a probe comprises a lens that is configured to collect and transmit light to a probe and/or a component thereof. As an example, the lens may be configured to collect and transmit light to an axis along the center and/or optical axis of the probe, along the center and/or optical axis of an optical fiber present in the probe, and/or along the center and/or optical axis of a fiber-optic bundle present in the probe.

In some embodiments, a probe is transparent to and/or may transmit light at a plurality of wavelengths (e.g., visible wavelengths, infrared wavelengths).

As described above, some probes described herein may be suitable substrates for performing assays. Such probes may be configured to be positioned proximal to a plurality of portions of the support structure and/or objects (e.g., fluids, objects containing fluids) supported by the support structure. This may be accomplished by translating the probe (e.g., vertically, in a first horizontal direction, in a second horizontal direction perpendicular to the first horizontal direction, in a combination of two or three of the preceding directions) and/or by translating the support structure (e.g., vertically, in a first horizontal direction, in a second horizontal direction, in a combination of two or three of the preceding directions). In some embodiments, an instrument may be configured such that it translates a probe through a pre-set program in which the probe is positioned at a plurality of locations for a plurality of times. It is also possible for an instrument to be configured such that an operator can translate the probe at will (e.g., an operator may be able to input a desired location to which the probe is translated location and/or to move the probe in real time by use of a controller). Additionally, some instruments may be configured such that they are not configured to translate a probe. In such embodiments, the probe may be stationary or immovable absent manual movement by an operator.

Pre-set programs may comprise some or all of the following sequential steps: translating the probe horizontally (e.g., in a first horizontal direction, in a second horizontal direction perpendicular to the first horizontal direction, in a combination of the two directions) until it is positioned above a container and/or a portion thereof (e.g., a well in a multi-well plate), either pausing for a defined amount of time (during which the container may be raised such that any fluid in the portion of the container, such as a well therein, contacts the probe) or lowering the probe until it contacts any fluid in the portion of the container (e.g., well), maintaining the probe in a position such that it contacts any fluid in the portion of the container (e.g., well) for a defined amount of time, and either pausing for a defined amount of time (during which the container may be lowered such that any fluid in the portion of the container, such as a well, no longer contacts the probe) or raising the probe until it no longer contacts any fluid in the portion of the container (e.g., well). Pre-set programs may repeat the above some or all of these sequential steps such that the probe sequentially contacts a plurality of fluids contained in a plurality of containers and/or portions thereof (e.g., a plurality of wells in a multi-well plate). Further examples of steps that pre-set programs may comprise include pre-wet (e.g., coating dissolution), initiation, calibration, reference, and/or shut-down steps.

In some embodiments, a probe comprises a surface that is functionalized and/or that has a surface chemistry that assists with the performance of an assay. The surface functionalization and/or chemistry may promote the formation of reaction products that are typically generated during assays thereon. For instance, the surface functionalization and/or chemistry may promote the bonding of one or more species generated during the assay to thereto. In some embodiments, a probe comprises a surface on which one or more reagents are immobilized. The reagent(s) may be immobilized on the probe in a variety of suitable manners. As an example, the reagent(s) may be bonded to the probe. The bonding may comprise covalent bonding, ionic bonding, polar bonding, van der Waals bonding, hydrophobic bonding, and/or hydrogen bonding.

In some embodiments, one or more reagents(s) may be immobilized on the probe in a manner such that they do not undergo significant (and/or any) detachment from the probe during the performance of assay. For instance, the reagent(s) may be immobilized on the probe in a manner that is stable to water, aqueous solutions, buffers, acids, bases, and/or bodily fluids. However, it is also possible for one or more reagents to be initially immobilized on a surface of a probe that are then released from the surface of the probe during the performance of an assay. As an example, a reagent that is initially immobilized on a surface of a probe may be configured to be released from the probe upon exposure to a particular stimulus. The stimulus may be present in a fluid.

Additionally or alternatively, it is possible for one or more reagent(s) to be immobilized on a probe in a manner such that the probe can be regenerated. It is also possible for a method to comprise regenerating a probe. Regeneration may comprise removing one or more reagent(s) from the probe. For instance, in some embodiments, regeneration comprises exposing a probe on which one or more reagent(s) are immobilized to a fluid (e.g., a buffer, such as an acidic buffer) that causes one or more of those reagent(s) to be detached from the probe. Afterwards, the probe may be exposed to a fluid comprising one or more new reagent(s) to be immobilized on the probe. Regenerating a probe may advantageously allow a probe to be employed during more than one assay (e.g., as a non-consumable). As an example, a first reagent and/or set of reagents may be immobilized on the probe prior to the performance of a first assay. These reagents may be configured to undergo a chemical reaction with one or more species possibly present during the assay. If this chemical reaction does occur, the probe may be unsuitable for performing another assay unless it is regenerated because the chemical reaction may render the reagent(s) unsuitable for engaging in further chemical reactions. Accordingly, after performance of the assay, the probe may be regenerated to yield a probe onto which a new reagent and/or set of reagents can be immobilized, thus allowing for the probe to be employed during the performance of further assays. The reagent and/or set of reagents may be the same reagent and/or set of reagents initially immobilized on the probe, or may differ in one or more ways (e.g., if an operator desires to employ the probe to perform a different assay).

It is also possible for some probes to not be regenerated and/or to be incapable of regeneration. Such probes may be employed as consumables.

A variety of suitable reagents may be immobilized on the surfaces of the probes described herein. Some reagents may be species that are capable of that engaging in one or more chemical reactions (e.g., one or more chemical reactions that may take place during an assay that the probe is employed to facilitate). For instance, a probe may comprise a reagent that is capable of bonding with another species (e.g., covalently, ionically, by polar interactions, by van der Waals interactions, hydrophobically, by hydrogen bonding, by complexing), absorbing another species, adsorbing another species, catalyzing a reaction of another species and/or between two or more species, decomposing (e.g., upon exposure to another species), undergoing a conformational shift, and/or catalyzing a reaction. In some embodiments, one or more of the previously described chemical reactions may cause the species with which the reagent reacts to become immobilized thereon. Selected non-limiting examples of suitable reagents include biomolecules (e.g., proteins, glycoproteins, peptides, nucleic acids (e.g., DNA), antibodies, antigens, polysaccharides, carbohydrates, hormones), ligands, small molecules, viruses, cells, inorganic compounds, sequestration compounds, capsids, and bacteria.

In some embodiments, a reagent immobilized on a surface of a probe is suitable for engaging in a chemical and/or biological reaction that comprises binding. It is also possible for a probe to be suitable for engaging in a chemical and/or biological reaction that does not comprise binding. When present, binding may comprise a reaction between a target and a binding partner that specifically binds to the target (e.g., an agent or molecule that specifically binds to the target). Binding may also comprise immobilizing a target on the binding partner. In some embodiments, the binding partner may specifically bind to an epitope on the target molecule. Non-limiting examples of specific pairs of binding partners and targets include an antibody and an antigen, an antibody fragment and an antigen, an antibody and a hapten, an antibody and a peptide, an antibody and a small molecule, an antigen and a fusion protein, an antibody fragment and a hapten, an enzyme and an enzymatic substrate, an enzyme and an inhibitor, an enzyme and a cofactor, a binding protein and a substrate, a carrier protein and a substrate, a protein and a small molecule, lecithin and a carbohydrate, a receptor and a hormone, a receptor and an effector, complementary strands of nucleic acid, a protein in combination with a nucleic acid repressor and an inducer, a ligand and a cell surface receptor, a virus and a ligand, and a receptor and a ligand.

Non-limiting examples of antibodies that may be binding partners or antibodies include intact (i.e., full-length) polyclonal and monoclonal antibodies, antigen-binding fragments of polyclonal and monoclonal antibodies (such as Fab, Fab', F(ab')2, or Fv), single chains (scFv), mutants of single chains, fusion proteins comprising an antibody portion, humanized antibodies, chimeric antibodies, diabodies, linear antibodies, single chain antibodies, multispecific antibodies (e.g., bispecific antibodies), and modified configurations of the immunoglobulin molecule that comprise an antigen recognition site of the required specificity. Non-limiting examples of antibodies falling into the last category include glycosylation variants of antibodies, amino acid sequence variants of antibodies, and covalently modified antibodies. Additionally, a binding partner may be an antibody of any class, such as IgD, IgE, IgG, IgA, or IgM (or sub-class thereof, e.g., IgG1, IgG2, IgG3, IgG4, IgA1 and/or IgA2.

An antigen may be a molecule or a portion of a molecule that can have antibodies generated against it. Antigens may be peptides, polysaccharides and/or lipids. Some antigens may originate from within the body (a "self-antigen"), and some antigens may originate from the external environment (a "non-self-antigen").

In some embodiments, antibodies suitable for performing a chemical and/or biological reaction specifically bind to epitopes on their target molecules. An epitope (which may be referred to as an antigenic determinant) may be the part of the antigen recognized (or bound by) an antibody. For example, the epitope may be the specific piece of the antigen to which an antibody binds. The part of an antibody that binds to the epitope may be referred to as a paratope. An epitope may be a conformational epitope (composed of discontinuous amino acids or sections of the antigen) or a linear epitope (composed of continuous amino acids). Some proteins may share segments of high sequence homology and/or structural similarity. These similar proteins may have common epitopes (in other words, the epitopes on different antibodies may be bound by the same antibody). Further, a protein that has been processed differentially (such as a protein that has gone a further enzymatic process) may share some, but not all epitopes with its pre-processing form. Non-limiting examples of different epitopes that may be added or removed during processing include N-terminal signal peptides (as seen, for example, on pre-pro-peptides) and changes seen when an inactive protein (e.g., a pro-peptide) is turned into an active form by post-translational modification.

When an antibody specifically binds to an epitope, it may engage in a binding reaction that is capable of discriminating between a target molecule and a non-target molecule. For example, a binding partner may specifically bind to a target molecule with greater than or equal to 2-fold greater affinity than to a non-target molecule with greater than or equal to 4-fold, greater than or equal to 5-fold, greater than or equal to 6-fold, greater than or equal to 7-fold, greater than or equal to 8-fold, greater than or equal to 9-fold, greater than or equal to 10-fold, greater than or equal to 20-fold, greater than or equal to 25-fold, greater than or equal to 50-fold, or greater than or equal to 100-fold greater affinity than to a non-target molecule.

The binding affinity of an antibody may be parametrized by its apparent association constant or $K_A$. The $K_A$ is the reciprocal of the dissociation constant ($K_D$). In some embodiments, a binding partner described herein has a dissociation constant ($K_D$) of greater than or equal to $10^{-5}$ M, greater than or equal to $10^{-6}$ M, greater than or equal to $10^{-7}$ M, greater than or equal to $10^{-8}$ M, greater than or equal to $10^{-9}$ M, or greater than or equal to $10^{-10}$ M. An increased binding affinity ($K_A$) corresponds to a decreased dissociation constant ($K_D$). Higher affinity binding of a binding partner (e.g., an antibody) to a first molecule relative to a second molecule can be indicated by a higher $K_A$ (or a smaller numerical value $K_D$) for binding to the first target than the $K_A$ (or numerical value $K_D$) for binding to the second target. In such cases, the antibody has a specificity for the first molecule (e.g., a protein in a first conformation or mimic thereof) relative to the second molecule (e.g., the same protein in a second conformation or mimic thereof, or a second protein). Differences in binding affinity (e.g., specificity) can be greater than or equal to 1.5-fold, greater than or equal to 2-fold, greater than or equal to 3-fold, greater than or equal to 4-fold, greater than or equal to 5-fold, greater than or equal to 10-fold, greater than or equal to 15-fold, greater than or equal to 20-fold, greater than or equal to 37.5-fold, greater than or equal to 50-fold, greater than or equal to 70-fold, greater than or equal to 80-fold, greater than or equal to 90-fold, greater than or equal to 100-fold, greater than or equal to 500-fold, greater than or equal to 1000-fold, greater than or equal to 10,000-fold, greater than or equal to $10^5$-fold.

In some embodiments, a reagent may be immobilized on a surface of a probe via a covalent bond. Prior to such immobilization, the surface of the probe may be functionalized such that it comprises a plurality of functional groups suitable for forming such covalent bonds. For instance, the surface of the probe may be functionalized by reaction with a bifunctional reagent comprising a siloxane group that facilitates attachment to the probe and a functional group that facilitates the formation of a covalent bond with the reagent to be immobilized on the probe. As another example, the surface of the probe may be exposed to a plasma or other treatment that generates functional groups in situ that facilitate the formation of a covalent bond with the reagent to be immobilized on the probe. Non-limiting examples of suitable types of functionals group that facilitate the formation of a covalent bond with the reagent to be immobilized on the probe include hydroxyls, amines, and carboxyls.

The probes described herein may be formed from a variety of suitable materials. In some embodiments, a probe comprises a glass and/or a polymer. Non-limiting examples of suitable glasses include $SiO_2$ and $Ta_2O_5$. Non-limiting examples of suitable polymers include polystyrene and polyethylene.

As described above, in some embodiments, an instrument comprises a support structure. The support structure may be configured to support one or more fluids and/or solids employed in an assay and/or may be configured to support a container for one or more fluids and/or solids employed in an assay. As an example, in some embodiments, a support structure is configured to support and/or receive a multi-well plate. As further examples, a support structure may be configured to support a microtiter plate, a glass slide, a droplet array, a vial, a microfluidic device, a microfluidic array, a microarray, and/or a digital microfluidic chip. In some embodiments, a container for fluids and/or solids is positioned on the support structure.

In some embodiments, a support structure is configured to be translated by an instrument of which it forms a part (e.g., vertically, in a first horizontal direction, in a second horizontal direction, in a combination of two or three of the preceding directions). In some embodiments, an instrument may be configured such that it translates a support structure through a pre-set program in which the support structure is positioned at a plurality of locations for a plurality of times. It is also possible for an instrument to be configured such that an operator can translate the support structure at will (e.g., an operator may be able to input a desired location to which the probe is translated location and/or to move the probe in real time by use of a controller). Additionally, some instruments may be configured such that they are not configured to translate a support structure. In such embodiments, the support structure may be stationary or immovable absent manual movement by an operator.

As described above, in some embodiments, an instrument comprises an optical detector. The optical detector may be configured to detect an optical signal and/or a method may comprise detecting an optical signal. An optical signal may be indicative of a feature of a sample being assayed (e.g., the presence, concentration, or absence of one or more components therein), indicative of a feature of a standard present in an assay (e.g., the presence, concentration, or absence of one or more components therein), a reference signal, a background signal, and/or a baseline signal.

Optical signals may comprise light or the absence of light. As an example of the former, the presence, intensity, and/or polarization of light may convey information about an assay being performed. For instance, some assays may result in the generation of light at a particular wavelength, within a particular wavelength range, at a particular combination of wavelengths, and/or having a particular polarization. The detection of such light may indicate that the assay was performed correctly, that the sample being assayed has a particular feature, and/or that the sample comprises a particular component in a particular amount. The absence of such light may indicate that the assay was performed incorrectly, that the sample being assayed lacks a particular feature, and/or that the sample lacks a particular component.

Light that is present in an optical signal may comprise light that has been emitted by fluorescence, luminescence (e.g., chemiluminescence), and/or scattering (e.g., Raman scattering). It is also possible for light that is present in an optical signal to comprise light that has been reflected or transmitted. In some embodiments, light that is present in an optical signal comprises light that has been polarized.

Optical signals may arise from a variety of locations in a fluid or solid. For instance, some optical signals may arise from a surface of a fluid or solid (e.g., an upper surface, a lower surface, a side surface). As another example, some optical signals may arise from an interior of a fluid or solid. In some embodiments, an optical signal arises from the entirety of the fluid or solid.

In some embodiments, the absence of light may convey information about an assay being performed. The assay may result in the generation of a species that absorbs light at a particular wavelength, within a particular wavelength range, and/or at a particular combination of wavelengths. The absence of such light may indicate that the assay was performed correctly, that the sample being assayed has a particular feature, and/or that the sample comprises a particular component in a particular amount. The presence of such light may indicate that the assay was performed incorrectly, that the sample being assayed lacks a particular feature, and/or that the sample lacks a particular component.

Light that is absent, and forms an optical signal, may comprise light that has been absorbed or reflected. It may be perceived as a change in color of the light impinging on the relevant fluid.

An optical signal may comprise the presence or absence of light of a variety of wavelengths and/or polarizations. In some embodiments, the light may comprise visible light. It is also possible for the light to comprise infrared light. Additionally, the light may be polarized light or unpolarized light.

Detection of optical signals may comprise detecting and/or determining a variety of suitable features thereof. In some embodiments, detecting an optical signal comprises detecting the presence or absence of light as described above. It is also possible for detecting an optical signal to comprise detecting the intensity and/or polarization of light as described above. Such detection may be performed at one or more discrete points in time or over a period of time. Additionally, such detection may be performed in a manner that yields a single data point (e.g., an endpoint, the average intensity of light at a particular wavelength as measured over a period of time, the average intensity of light at a particular wavelength as computed by averaging a plurality of measurements of light intensity, the intensity of light at a particular wavelength as determined from a single measurement), a plurality of data points. The plurality of data points may describe the variation of the optical signal over time (e.g., in a kinetic measurement), the variation of the optical signal as a function of position (e.g., across multiple positions in a single fluid, such as a single sample or a single standard), and/or the variation of the optical signal as a function of wavelength.

In some embodiments, a method comprises detecting two or more optical signals. These optical signals may comprise optical signals of the same type (e.g., they may comprise the same type of light detected in the same manner) and/or may comprise optical signals that differ in one or more ways. The two or more optical signals may arise from a single fluid or solid, may arise from more than one fluid or solid, and/or may comprise an optical signal that does not arise from any fluid or solid (e.g., an optical signal that is a reference signal, a background signal, and/or a baseline signal). In some embodiments, the two or more optical signals are associated with the same sample and/or are associated with assays performed on the same sample (but, in some embodiments, be associated with and/or arise from different probes and/or fluids and/or solids).

When present, the two or more optical signals may comprise at least two optical signals (of the same type and/or of different types) detected by optical detectors positioned at different locations and/or optically coupled to different locations (e.g., proximal to different locations in a container supported by a support structure, such as different wells in a multi-well plate; proximal to different containers). It is also possible for the two or more optical signals to comprise at least two optical signals (of the same type and/or of different types) detected by a single optical detector. Similarly, the two or more optical signals may comprise at least two optical signals (of the same type and/or of different types) detected at different points in time (e.g., at discrete points in time during an assay, over the course of a reaction occurring in a container) and/or to comprise at least two optical signals detected at a single point in time.

When a method comprises detecting two or more different types of optical signals, the optical signals may differ in a variety of ways. Non-limiting examples of such differences include the manner in which the light detected is generated (e.g., one optical signal may comprise light emitted by fluorescence and another may comprise light emitted by luminescence), the wavelength (or wavelength range) of light detected (e.g., one optical signal may comprise light emitted at a first wavelength and another may comprise light emitted at a second wavelength), and the wavelength (or wavelength range) or light absorbed (e.g., one optical signal may comprise light absorbed at a first wavelength and another may comprise light absorbed at a second wavelength). It is also possible for a method to comprise detecting optical signals comprising different types of light (e.g., one optical signal that comprises light that is emitted and another optical signal that comprises light that is scattered) and/or for a method to comprise detecting both an optical signal comprising light (e.g., that has been emitted, transmitted, reflected, scattered, and/or polarized) and an optical signal comprising the lack of light (e.g., that has been absorbed or reflected). One further specific example of a method comprising detecting two optical signals of different types is a method that comprises detecting two optical signals comprising light having different wavelengths and further comprises determining the ratio of these two wavelengths to each other.

One example of a method that comprises detecting two optical signals (of the same or different type) is a method that comprises detecting both: (1) a first optical signal that is indicative of a feature of a first sample; and (2) a second optical signal. The second optical signal may be any suitable type of optical signal. For instance, in some embodiments, the second optical signal is indicative of a second sample. It is also possible for the second optical signal to be indicative of a feature of a different type of fluid and/or solid, to not arise from any fluid or solid (e.g., in the case of an optical signal that is a reference signal, a background signal, and/or a baseline signal), to be indicative of a different feature of the first sample, and/or to be indicative of the same feature of the first sample. As one example, in some embodiments, a second optical signal is indicative of a feature of a standard (e.g., it may be a reference signal arising from a reference standard). Such optical signals may assist with calibrating an instrument and/or detecting if an instrument is functioning properly. It is also possible for a method to comprise comparing a signal indicative of a feature of a sample to a signal indicative of a feature of a standard. Such comparisons may be useful for subtracting out background noise and/or enhancing measurement reproducibility.

Other examples of methods that comprise detecting two optical signals (of the same or different type) include methods in which no optical signals arise from any samples. Such methods may be methods in which exclusively reference, background, and/or baseline optical signals are detected. In such embodiments, the method may comprise calibrating an instrument, assessing instrument functionality, and/or generating a set of data that may be employed to normalize and/or calibrate data obtained from samples.

As described above, in some embodiments, detection of an optical signal comprises detecting the location at which the optical signal was generated. This may be accomplished by detecting a position of a probe transmitting the optical signal to a detector and/or by detecting the location of a detector detecting the optical signal.

A variety of suitable optical detectors may be employed in the instruments described herein. For instance, non-limiting examples of suitable types of detectors include photon-counting devices, spectrophotometers, Raman spectrometers, infrared spectrometers, polarization detectors, photodiodes, CCD/CMOS sensors, and imaging sensors.

As described above, in some embodiments, an instrument comprises a light source. The light source may serve as a source of light that stimulates the emission of an optical signal.

In some embodiments, a light source supplies light at a plurality of wavelengths. For instance, an instrument may comprise a light source that comprises an incandescent bulb. As further examples, an instrument may comprise a light source that comprises a xenon lamp, a mercury lamp, and/or an arc lamp. When an instrument comprises a light source supplies light at a plurality of wavelengths, the instrument may further comprise one or more optical filters and/or monochromators. Such optical filter(s) and/or monochromator(s) may be positioned between the light source and the location of the species generating the optical signal, between the light source and the detector, between the detector and the location of the species generating the optical signal, between the optical detector and the probe, between the light source and the probe, and/or between an optical detector and an optical cable. The former may be beneficial if the light emitted by the light source comprises at least one wavelength that would overlap with the wavelength of the optical signal and/or if the light emitted by the light source comprises at least one wavelength that would stimulate the generation of an optical signal independently of whether the assay would yield a positive or negative result (e.g., in the case where light at the relevant wavelength would stimulate emission from a variety of species, including a species that would always be immobilized on the probe and/or present in a fluid contacting the probe).

In some embodiments, an instrument comprises a light source that emits light in a relatively narrow band of wavelengths. For instance, an instrument may comprise a laser light source and/or an LED light source.

The light sources described herein may also supply light at a single polarization and/or at a plurality of polarizations. When a light source supplies light at a plurality of polarizations, the instrument may further comprise one or more polarizing filters. Such polarizing filter(s) may be positioned between the light source and the location of the species generating the optical signal, between the light source and the detector, and/or between an optical detector and an optical cable. The former may be beneficial if the light emitted by the light source comprises light at a polarization that would overlap with the wavelength of the optical signal and/or if the light emitted by the light source comprises at least one polarization that would stimulate the generation of an optical signal independently of whether the assay would yield a positive or negative result (e.g., in the case where light at the relevant polarization would stimulate emission from a variety of species, including a species that would always be immobilized on the probe and/or present in a fluid contacting the probe). The former may also be beneficial if the optical signal comprises light polarized by a species immobilized on a probe and/or a species generated from a species immobilized on a probe.

Figure 7:
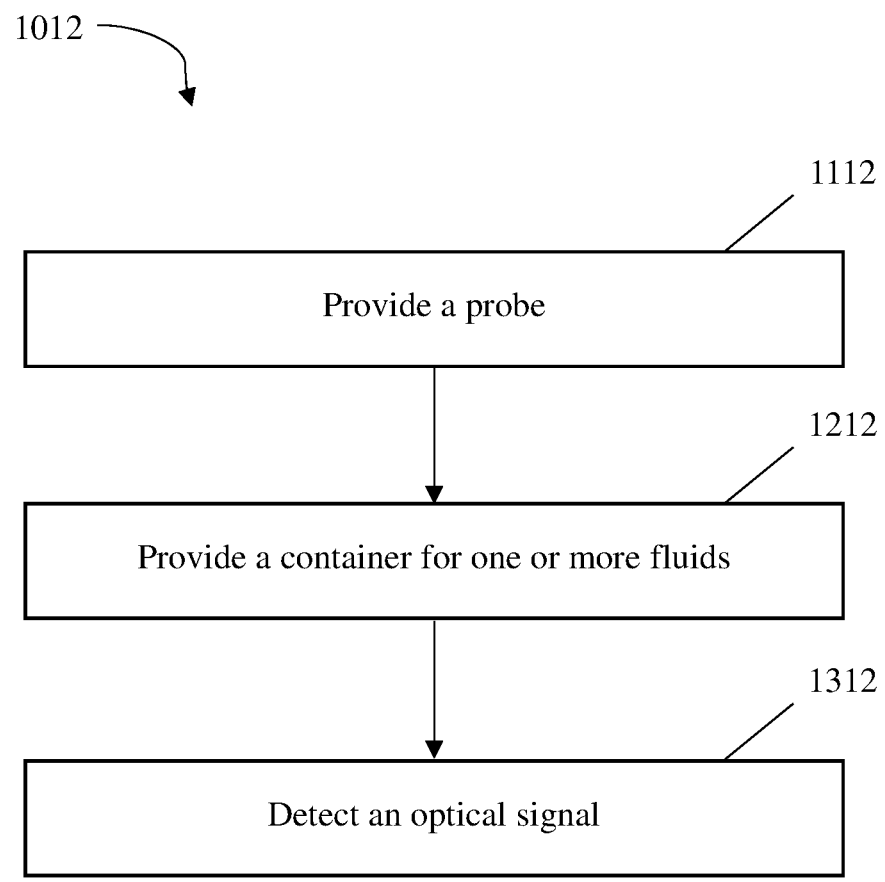
FIG. 7 is a schematic depiction of a method.

As described elsewhere herein, some instruments may be suitable for performing assays and some methods may comprise performing assays (e.g., with the use of an instrument described herein). In some embodiments, a method of performing an assay comprises providing a probe on which a reagent is immobilized and for which light is transmitted through one or more apertures thereon, providing a container for one or more fluids, and detecting an optical signal. The optical signal may comprise light that has been emitted, polarized, and/or scattered from a species immobilized on the probe, light that has been emitted, polarized, and/or scattered from a species generated from a species immobilized on the probe, the absence of light due to absorption of light by a species immobilized on the probe, and/or the absence of light due to absorption of light by a species generated from a species immobilized on the probe. This method is shown in a flow chart in FIG. 7. In FIG. 7, the method 1012 comprises the step 1112 of providing a probe, the step 1212 of providing a container for one or more fluids, and the step 1312 of detecting an optical signal. In some embodiments, the performance of an assay comprises performing more steps than those shown in FIG. 7, and in some embodiments an assay may be performed that lacks one or more of the steps shown in FIG. 7. Non-limiting examples of further steps that may be performed are described in further detail below.

In some embodiments, an assay comprises contacting a probe with (and, in some embodiments, subsequently removing a probe from contact with) one or more fluids. The probe may be removed from contact with each fluid with which it is in contact in the plurality of fluids before contacting the next fluid in the plurality of fluids. In some embodiments, removing a probe from contact with a fluid stops a reaction from occurring (e.g., a reaction between a species immobilized on a probe and a species present in the fluid from which the probe is removed). Stopping a reaction by removing a probe from contact with a fluid may be performed in response to an optical signal (e.g., an optical signal indicative of the fluid and/or a sample with which the probe was in contact prior to contacting the fluid). It is also possible for a reaction to be stopped by removing a probe from contact with a fluid after a preset interval has elapsed and/or by manual action of an operator.

In some embodiments, the performance of an assay comprises sequentially contacting a probe with a plurality of fluids and detecting an optical signal. The sequential contacting may be effectuated by translating the probe and/or a support structure. During assay performance, the optical signal may be associated with a species immobilized on the probe. As described elsewhere herein, the optical signal may comprise light emitted, transmitted, reflected, scattered, polarized, and/or absorbed by a species immobilized on a probe and/or may comprise light that is emitted, transmitted, reflected, scattered, polarized, and/or absorbed by a species that is generated from a species immobilized on a probe. In some embodiments, the optical signal is detected while the probe is in contact with a fluid in the plurality of fluids. It is also possible for the optical signal to be generated upon initial contact between the probe and a fluid in the plurality of fluids.

As also described elsewhere herein, some methods may comprise employing two probes to conduct a common assay and/or two probes to conduct two distinct assays (which may be of the same type and/or performed on the same sample). In such embodiments, a second probe may also be sequentially contacted with a second plurality of fluids and a second optical signal (e.g., comprising emitted, transmitted, reflected, polarized, and/or scattered light and/or the absence of light that has been absorbed and/or reflected) may be detected. The probe may be removed from contact with each fluid in the second plurality of fluids with which it is in contact before contacting the next fluid in the second plurality of fluids. In some embodiments, the second optical signal is detected while the probe is in contact with a fluid in the second plurality of fluids. The second probe may be employed to perform a second assay on the same sample on which the first probe performs the assay, may be employed to perform the same assay on the same sample on which the first probe performs the assay, and/or may be employed to perform an assay on a different sample (e.g., the same assay performed by the first probe, a different assay).

Some assays comprise detecting one or more qualitative features of a sample (e.g., the presence absence of a species of interest, such as a protein). Some assays comprise detecting one or more quantitative features of a sample (e.g., the amount of a species of interest present in the sample, such as the amount of a protein present in the sample). In some embodiments, an assay comprises performing a kinetic measurement (e.g., the rate of binding of a species in a fluid, such as a sample, to a reagent immobilized on a probe) and/or a pulse measurement. In some embodiments, an assay comprises performing a pulse measurement, such as a measurement performed during a flash luminescence reaction and/or a flash reaction. Some suitable flash luminescence reactions and flash reactions comprise contacting a probe with a species immobilized thereon that is a catalyst for a reaction and then measuring an optical signal associated with a species generated by that reaction.

A variety of suitable assays may be performed, non-limiting examples of which include ELISA assays (e.g., direct ELISA assays, indirect ELISA assays, sandwich ELISA assays), whole cell assays, and biomolecular interaction assays. Some assays may comprise detecting cell surface proteins, empty capsids, and/or capsids containing nucleic acids.

In some embodiments, an assay is performed on a sample. In such embodiments, at least one plurality of fluids employed during the assay may comprise a fluid that is a sample. The sample may be one fluid in a plurality of fluids with which a probe is contacted and/or may be present in (e.g., suspended in, dissolved in) one fluid in a plurality of fluids with which a probe is contacted. It is also possible for two or more (or each) pluralities of fluids employed in an assay to comprise a fluid that is a sample (e.g., in the case where performing the assay comprises employing two or more probes to each contact its own plurality of samples). In some embodiments, performing an assay comprises contacting at least one probe with at least one plurality of fluids that lack any fluids that are samples.

Some samples may comprise bodily fluids and/or biological materials. As an example, in some embodiments, a sample comprises cells (e.g., live cells) and/or reagents (e.g., biomolecules). Samples may comprise some or all of the reagents described elsewhere herein with respect to the reagents that may be immobilized on the surface of a probe and/or may comprise reagents other than those so described. Non-limiting examples of some reagents that may be included in samples suitable for being analyzed by an assay include proteins, glycoproteins, peptides, ligands, antibodies, antigens, hormones, nucleic acids (e.g., DNA), polysaccharides, carbohydrates, small molecules, inorganic compounds, sequestration compounds, viruses, capsids, cells, and bacteria.

In some embodiments, a sample comprises a component that becomes immobilized on the probe during performance of the assay and/or is configured to become immobilized on the probe during performance of the assay. For instance, in some embodiments, a sample comprises a component that binds to the probe and/or is configured to bind to the probe. It is also possible for the performance of an assay to determine whether or not a sample comprises such components. For instance, in some embodiments, a sample may comprise an antigen for an antibody immobilized on a probe. Performing the assay may identify whether the sample in fact comprises an antigen and/or the concentration of such an antigen in the sample. As further examples, as described above, a reagent may be immobilized on a surface of a probe that is suitable for engaging in a chemical and/or biological reaction that comprises binding, and the sample may comprise a binding partner and/or target for that reagent. For instance, an antigen may be immobilized on the surface of a probe and the sample may comprise an antibody for that antigen (e.g., an enzyme-linked antibody for that antigen).

It is also possible for an assay to be performed on a standard. For instance, in some embodiments, an assay is performed on a positive standard and/or a negative standard. Positive standards may be configured to always yield an optical signal and/or to always yield an optical signal at a known intensity and/or polarization if the assay is performed correctly. Some positive standards comprise a known concentration of a reagent to be detected by the assay. Negative standards may be configured to always yield no optical signal if the assay is performed correctly. Some positive standards lack a reagent to be detected by the assay. The performance of an assay on a positive standard and/or a negative standard may be useful for calibrating the results obtained from an assay performed on a sample and/or to confirm that an instrument is performing properly. Some embodiments may comprise contacting a first probe with a plurality of fluids that comprises a sample (and, optionally, lacks a standard) and a second probe with a plurality of fluids that comprises a standard (and, optionally, lacks a sample). It is also possible for an embodiment to comprise contacting two or more standards (e.g., with two or more probes, in a manner such that each probe contacts a single standard), such as both a positive standard and a negative standard and/or two or more positive standards comprising differing concentrations of a reagent to be detected by the assay.

Fluids other than samples and standards that may be present during the performance of an assay include fluids that comprise species that assist with the performance of the assay. As an example, fluids that comprise one or more reagents (e.g., one or more reagents of the type described elsewhere herein with respect to the types of reagents that may be immobilized on probes) may be present. Such fluids may be provided separately from any samples and/or standards (e.g., in a separate well in a multi-well plate). Additionally, such fluids may comprise a reagent configured to be immobilized on a species immobilized on a probe. As one example, such fluids may comprise a reagent configured to be immobilized on a species initially immobilized on a probe. The reagent present in the fluid may be a reagent that is configured to undergo a reaction with a species that may be present in a sample. The reaction may comprise immobilizing the reagent present in the sample thereon (i.e., on the species initially present in the fluid). As another example, a fluid may comprise a reagent that is configured to be immobilized on a reagent initially present in a sample. Such a reagent may be immobilized on the probe via the reagent initially present in the sample. Such a reagent may be configured to generate an optical signal and/or to react with a further reagent to generate an optical signal.

Non-limiting examples of reagents that may be present in fluids described herein and/or configured to be immobilized on a species immobilized on a probe include ligands (e.g., ligands for analytes present in the sample), binding partners and/or targets for analytes present in samples, antibodies (e.g., antibodies for antigens present in the sample, enzyme-linked antibodies, primary enzyme-linked antibodies, secondary enzyme-linked antibodies, enzyme-linked antibodies for antigens present in samples, antibodies comprising fluorophores), proteins, glycoproteins, peptides, nucleic acids, antigens, polysaccharides, carbohydrates, hormones, small molecules, viruses, cells, inorganic compounds, sequestration compounds, capsids, and bacteria. In some embodiments, a reagent comprises an enzyme and/or is bonded to an enzyme. Non-limiting examples of suitable enzymes include horseradish peroxidase and alkaline phosphatase.

In some embodiments, a fluid that comprises one or more reagents configured to generate an optical signal is present during the performance of an assay. Such fluids may be provided separately from any samples, standards, and/or fluids comprising species that assist with the performance of the assay (e.g., in a separate well in a multi-well plate), one or more reagents, and/or fluids comprising species that assist with the performance of the assay. One example of such a fluid is a fluid that comprises a reagent that is configured to react with a reagent immobilized on a probe (e.g., a reagent initially present in a sample, a reagent immobilized on a reagent initially present in the sample). Reagents configured to react with reagents immobilized on a probe may generate an optical signal upon undergoing such a reaction. For instance, a fluid may comprise a reagent configured to undergo a reaction with a species immobilized on a probe that generates a species that absorbs light, transmits light, reflects light, fluoresces light, undergoes scattering (e.g., Raman scattering), is polarized, and/or undergoes luminescence (e.g., chemiluminescence). In some embodiments, an optical signal is detected while a probe is in contact with a fluid that comprises one or more reagents configured to generate an optical signal and/or upon initial contact with such a fluid.

Non-limiting examples of reagents that may be configured to generate an optical signal include enzyme substrates (e.g., for enzyme-linked antibodies). Some methods comprise reacting an enzyme substrate with an enzyme (e.g., an enzyme-linked antibody). Such a reaction may result in the generation of products of an enzymatic reaction, one or more of which may be capable of and/or configured to generate an optical signal.

In some embodiments, one or more wash fluids is present during the performance of an assay. Wash fluids may be provided separately from any samples, standards, fluids comprising species that assist with the performance of the assay, and/or fluids comprising reagents configured to generate an optical signal (e.g., in a separate well in a multi-well plate), one or more standards, one or more reagents, fluids comprising species that assist with the performance of the assay, and/or fluids comprising reagents configured to generate an optical signal. A wash fluid may be a fluid that is configured to remove species that are weakly adhered to a probe. Removing such species from a probe may enhance the reproducibility of the assay by eliminating signal from a species that is not immobilized on thereon. Additionally, removing such species from a probe may reduce cross-contamination between different fluids present during the assay. One example of a suitable wash fluid is a wash buffer (e.g., a glycin buffer, a phosphoric acid buffer).

In some embodiments, an assay is conducted by sequentially contacting a probe on which a reagent is immobilized with the following fluids: a sample comprising a first reagent configured to be immobilized on the probe, a fluid comprising a second reagent configured to become immobilized on the first reagent, and a fluid comprising a third reagent configured to react with the second reagent to generate a species that generates an optical signal. As another example, an assay may comprise sequentially contacting a probe on which a reagent is immobilized with the following fluids: a sample comprising a first reagent configured to be immobilized on the probe, a fluid comprising a second reagent configured to become immobilized on the first reagent, a fluid comprising a third reagent configured to become immobilized on the second reagent, and a fluid comprising a fourth reagent configured to react with the third reagent to generate a species that generates an optical signal. It is also possible for a process to be performed in which a standard is the first fluid contacted by the probe but for which the other steps are the same as those in one of the preceding two sentences. Additionally, some methods may comprise contacting a probe with a wash fluid (e.g., a wash buffer) in between two or more of pairs of the steps described above.

The fluids employed during the assays described herein may be contained in a variety of suitable containers. In some embodiments, some or all of such fluids are contained in one or more multi-well plates. In such embodiments, the fluids may be contained in separate wells. The wells may be in a single common row, a common set of rows, a single common column, or a common set of columns. In embodiments in which two or more pluralities of fluid are contacted by two or more probes, each plurality of fluids may be positioned as described above (e.g., each plurality of fluids may be positioned in a single common row, a common set of rows, a single common column, or common set of columns). In some embodiments, a method comprises contacting a first probe with a first plurality of fluids that are positioned in a single column or row and contacting a second probe with a second plurality of fluids that are positioned in a different row or column. It is also possible for a method to comprise contacting a probe with a plurality of fluids that are positioned in two or more columns or two or more rows. It is also possible for the fluids to be contained in other types of articles as described elsewhere herein. During performance of the assay, a probe may be translated across one or more containers containing a plurality of fluids and/or a support structure on which one or more such container(s) are supported may be translated with respect to a probe. For instance, in the case of a multi-well plate, a probe may be translated across a plurality of wells in the multi-well plate. Some or all of those wells may contain the fluids employed to perform the assay. As another example, a support structure on which a multi-well plate is supported may be translated so that a plurality of wells (some or all of which contain fluids suitable for performing the assay) are sequentially positioned proximal to a probe.

Performance of an assay may also comprise one or more steps and/or periods of time in which both a support structure and a probe are stationary, in which all parts of the instrument are stationary, in which two or more parts of the instrument are stationary with respect to each other, and/or in which two or more parts of the instrument (despite being non-stationary with respect to each other) do not experience appreciable net displacement from each other. As an example, in some embodiments, a method comprises one or more periods of time during which a probe is incubated with a fluid. The incubation may occur while both the probe and the fluid (and, possibly, a container containing the fluid and/or a support structure supporting such a container) are stationary. It is also possible for the incubation to occur while either the fluid (and, possibly, a container containing the fluid and/or a support structure supporting such a container) and/or the probe are shaking. In some embodiments, both the fluid (and, possibly, a container containing the fluid and/or a support structure supporting such a container) and the probe shake together. In some embodiments, incubation comprises agitating the fluid (e.g., a sample) and/or mixing the fluid. The agitation and/or mixing may be accomplished by stirring the fluid (e.g., with the probe).

It is also possible for incubation to comprise adjusting and/or maintaining the temperature of the fluid. For instance, incubation may comprise heating the fluid and/or cooling the fluid.

In some embodiments, an optical signal may be generated and/or detected during one or more steps and/or periods of time in which both a support structure and a probe are stationary, in which all parts of the instrument are stationary, in which two or more parts of the instrument are stationary with respect to each other, and/or in which two or more parts of the instrument (despite being non-stationary with respect to each other) do not experience appreciable net displacement from each other. The detection may occur during incubation and/or in the absence of incubation.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of." will refer to the inclusion of exactly one element of a number or list of elements. In general, the term "or" as used herein shall only be interpreted as indicating exclusive alternatives (i.e. "one or the other but not both") when preceded by terms of exclusivity, such as "either." "one of." "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An instrument for performing an assay, comprising:
a probe;
a support structure positioned proximal to the probe, wherein a container for one or more fluids is positioned on the support structure; and
an optical detector configured to detect an optical signal, wherein:
a reagent is immobilized on the probe,
the probe is capable of being translated by the instrument between a plurality of locations at which a plurality of fluids are positioned, and
the optical signal comprises:
light that has been emitted and/or transmitted from a species immobilized on the probe,
light that has been emitted, transmitted, reflected, and/or scattered from a species generated from a species immobilized on the probe,
the absence of light due to absorption of light by a species immobilized on the probe, and/or
the absence of light due to absorption of light by a species generated from a species immobilized on the probe.

2. The instrument of claim 1, wherein the probe transmits light through one or more apertures, wherein the instrument comprises an optical cable, and wherein the one or more apertures are positioned on a side of the probe opposite the optical cable.

3. The instrument of claim 1, wherein a monochromator is positioned between a light source and the probe.

4. The instrument of claim 1, wherein the optical detector is not coupled to the probe by an optical cable.

5. The instrument of claim 1, wherein the container comprises a multi-well plate.

6. The instrument of claim 1, wherein the instrument further comprises a second probe, and wherein the second probe is capable of being translated independently of the probe.

7. The instrument of claim 1, wherein the instrument further comprises a second optical detector.

8. The instrument of claim 1, wherein the container contains one or more of the plurality of fluids.

9. An instrument for performing an assay, comprising:
a housing;
an optical cable, and
an optical detector configured to detect an optical signal, wherein:
the housing comprises a component capable of receiving a probe,
the probe transmits light through one or more apertures,
the one or more apertures are positioned on a side of the probe opposite the optical cable,
the housing comprises a support structure positioned proximal to the component capable of receiving the probe,
the support structure is configured to receive a container for one or more fluids,
the instrument is capable of translating the probe between a plurality of locations proximal to a plurality of locations in the container,
the optical cable transmits the light to the optical detector, and
the optical signal comprises:
light that has been emitted and/or transmitted from a species immobilized on the probe,
light that has been emitted, transmitted, reflected, and/or scattered from a species generated from a species immobilized on the probe,
the absence of light due to absorption of light by a species immobilized on the probe, and/or
the absence of light due to absorption of light by a species generated from a species immobilized on the probe.

10. An instrument for performing an assay, comprising:
a probe;
a support structure positioned proximal to the probe, wherein a container for one or more fluids is positioned on the support structure; and
an optical detector configured to detect an optical signal, wherein:
a reagent is immobilized on the probe,
the support structure is capable of being translated by the instrument such that a plurality of portions of the support structure are sequentially positioned proximal to the probe, and
the optical signal comprises:
light that has been emitted and/or transmitted from a species immobilized on the probe,
light that has been emitted, transmitted, reflected, and/or scattered from a species generated from a species immobilized on the probe,
the absence of light due to absorption of light by a species immobilized on the probe, and/or
the absence of light due to absorption of light by a species generated from a species immobilized on the probe.

11. A method of performing an assay, comprising:
sequentially contacting a probe with a plurality of fluids by translating the probe across a plurality of wells containing the plurality of fluids; and
detecting an optical signal, wherein:
a reagent is immobilized on the probe, and
the optical signal comprises:
light that has been emitted and/or transmitted from a species immobilized on the probe,
light that has been emitted, transmitted, reflected, and/or scattered from a species generated from a species immobilized on the probe,
the absence of light due to absorption of light by a species immobilized on the probe, and/or
the absence of light due to absorption of light by a species generated from a species immobilized on the probe.

12. The method of claim 11, further comprising sequentially contacting the probe with a second plurality of fluids.

13. The method of claim 11, wherein the method comprises:
exposing the probe to a first fluid, thereby causing the reagent to be detached from the probe; and
subsequently, exposing the probe a second fluid comprising a new reagent, thereby causing the new reagent to be immobilized on the probe.

14. An instrument for performing an assay, comprising:
an optical detector configured to detect an optical signal;
a probe, wherein the probe is configured to transmit light from a light source to a fluid positioned proximal to the probe, the probe is configured to transmit light from an optical cable to a fluid positioned proximal to the probe, the probe is configured to transmit light from a fluid positioned proximal to the probe to the optical detector, and/or the probe is configured to transmit light from a fluid positioned proximal to the probe to an optical cable;
a support structure positioned proximal to the probe, wherein:
a reagent is immobilized on the probe,
the probe is capable of being horizontally translated by the instrument between a plurality of locations at which a plurality of fluids are positioned, and
the optical signal comprises:
light that has been emitted and/or polarized from a species immobilized on the probe,
light that has been emitted, polarized and/or scattered from a species generated from a species immobilized on the probe,
the absence of light due to absorption of light by a species immobilized on the probe, and/or
the absence of light due to absorption of light by a species generated from a species immobilized on the probe.

15. The instrument of claim 14, wherein the plurality of fluids comprises the fluid proximal to the probe to which the probe is configured to transmit light from the light source, the fluid proximal to the probe to which the probe is configured to transmit light from the optical cable, the fluid proximal to the probe from which the probe is configured to transmit light to the optical detector, and/or the fluid positioned proximal to the probe from which the probe is configured to transmit light to the optical cable.

16. An instrument for performing an assay, comprising:
an optical detector configured to detect an optical signal;
a housing; and
a probe, wherein the probe is configured to transmit light from a light source to a fluid positioned proximal to the probe, the probe is configured to transmit light from an optical cable to a fluid positioned proximal to the probe, the probe is configured to transmit light from a fluid positioned proximal to the probe to the optical detector, and/or the probe is configured to transmit light from a fluid positioned proximal to the probe to an optical cable, wherein:
the housing comprises a component capable of receiving the probe,
a reagent is immobilized on the probe,
the housing comprises a support structure positioned proximal to the component capable of receiving the probe,
the support structure is configured to receive a container for one or more fluids,
the instrument is capable of horizontally translating the probe between a plurality of locations proximal to a plurality of locations in the container, and
the optical signal comprises:
light that has been emitted and/or polarized from a species immobilized on the probe,
light that has been emitted, polarized, and/or scattered from a species generated from a species immobilized on the probe,
the absence of light due to absorption of light by a species immobilized on the probe, and/or
the absence of light due to absorption of light by a species generated from a species immobilized on the probe.

17. The instrument of claim 16, wherein the container contains the fluid proximal to the probe to which the probe is configured to transmit light from the light source, the fluid proximal to the probe to which the probe is configured to transmit light from the optical cable, the fluid proximal to the probe from which the probe is configured to transmit light to the optical detector, and/or the fluid positioned proximal to the probe from which the probe is configured to transmit light to the optical cable.

18. An instrument for performing an assay, comprising:
an optical detector configured to detect an optical signal;
a probe, wherein the probe is configured to transmit light from a light source to a fluid positioned proximal to the probe, the probe is configured to transmit light from an optical cable to a fluid positioned proximal to the probe, the probe is configured to transmit light from a fluid positioned proximal to the probe to the optical detector, and/or the probe is configured to transmit light from a fluid positioned proximal to the probe to an optical cable; and
a support structure positioned proximal to the probe, wherein:
a reagent is immobilized on the probe,
a container for one or more fluids is positioned on the support structure,
the support structure is capable of being translated by the instrument such that a plurality of portions of the support structure are sequentially positioned proximal to the probe, and
the optical signal comprises:
light that has been emitted and/or polarized from a species immobilized on the probe,
light that has been emitted, polarized, and/or scattered from a species generated from a species immobilized on the probe,
the absence of light due to absorption of light by a species immobilized on the probe, and/or
the absence of light due to absorption of light by a species generated from a species immobilized on the probe.

19. The instrument of claim 18, wherein the container contains the fluid proximal to the probe to which the probe is configured to transmit light from the light source, the fluid proximal to the probe to which the probe is configured to transmit light from the optical cable, the fluid proximal to the probe from which the probe is configured to transmit light to the optical detector, and/or the fluid positioned proximal to the probe from which the probe is configured to transmit light to the optical cable.

20. An instrument for performing an assay, comprising:
an optical detector configured to detect an optical signal;
a housing; and
a probe, wherein the probe is configured to transmit light from a light source to a fluid positioned proximal to the probe, the probe is configured to transmit light from an optical cable to a fluid positioned proximal to the probe, the probe is configured to transmit light from a fluid positioned proximal to the probe to the optical detector, and/or the probe is configured to transmit light from a fluid positioned proximal to the probe to an optical cable, wherein:
a reagent is immobilized on the probe,
the housing comprises a component capable of receiving a probe,
the housing comprises a support structure positioned proximal to the component capable of receiving the probe,
a container for one or more fluids is positioned on the support structure,
the container comprises a multi-well plate, the support structure is configured to receive the container, the support structure is capable of being translated by the instrument such that a plurality of locations in the container are sequentially positioned proximal to the probe when the probe is positioned in the component, and the optical signal comprises:
- light that has been emitted and/or polarized from a species immobilized on the probe,
- light that has been emitted, transmitted, reflected, and/or scattered from a species generated from a species immobilized on the probe,
- the absence of light due to absorption of light by a species immobilized on the probe, and/or
- the absence of light due to absorption of light by a species generated from a species immobilized on the probe.

21. The instrument of claim 20, wherein the container contains the fluid proximal to the probe to which the probe is configured to transmit light from the light source, the fluid proximal to the probe to which the probe is configured to transmit light from the optical cable, the fluid proximal to the probe from which the probe is configured to transmit light to the optical detector, and/or the fluid positioned proximal to the probe from which the probe is configured to transmit light to the optical cable.

22. A method, comprising:
providing a probe;
providing a container for one or more fluids, wherein the container is positioned on a support structure; and
detecting an optical signal, wherein:
 a reagent is immobilized on the probe,
 light is transmitted through one or more apertures on the probe, and
 the optical signal comprises:
 - light that has been emitted and/or polarized from a species immobilized on the probe,
 - light that has been emitted, polarized, and/or scattered from a species generated from a species immobilized on the probe,
 - the absence of light due to absorption of light by a species immobilized on the probe, and/or
 - the absence of light due to absorption of light by a species generated from a species immobilized on the probe.

23. The method of claim 22, further comprising sequentially contacting the probe with a plurality of fluids, and wherein sequentially contacting the probe with the plurality of fluids comprises translating a plurality of wells containing the plurality of fluids proximal to the probe.

* * * * *